(12) United States Patent
Horiuchi et al.

(10) Patent No.: US 11,069,057 B2
(45) Date of Patent: Jul. 20, 2021

(54) SKIN DIAGNOSTIC DEVICE AND SKIN DIAGNOSTIC METHOD

(71) Applicant: PANASONIC INTELLECTUAL PROPERTY MANAGEMENT CO., LTD., Osaka (JP)

(72) Inventors: Koji Horiuchi, Fukuoka (JP); Tadanori Tezuka, Fukuoka (JP); Hiroto Tomita, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 168 days.

(21) Appl. No.: 16/303,430

(22) PCT Filed: Apr. 24, 2017

(86) PCT No.: PCT/JP2017/016128
§ 371 (c)(1),
(2) Date: Nov. 20, 2018

(87) PCT Pub. No.: WO2017/203913
PCT Pub. Date: Nov. 30, 2017

(65) Prior Publication Data
US 2020/0320683 A1 Oct. 8, 2020

(30) Foreign Application Priority Data
May 25, 2016 (JP) .............................. JP2016-104307

(51) Int. Cl.
*G06T 7/00* (2017.01)
*G06T 7/90* (2017.01)
(Continued)

(52) U.S. Cl.
CPC .......... *G06T 7/0012* (2013.01); *A61B 5/0077* (2013.01); *A61B 5/1032* (2013.01);
(Continued)

(58) Field of Classification Search
CPC .................... G06T 7/0012; G06T 7/90; G06T 2207/10024; G06T 2207/30088;
(Continued)

(56) References Cited

U.S. PATENT DOCUMENTS

2004/0028263 A1 2/2004 Sakamoto
2014/0088440 A1 3/2014 Swart et al.
(Continued)

FOREIGN PATENT DOCUMENTS

CN 1675919 B * 10/2010 ......... H04N 9/04557
FR 2984721 A1 6/2013
(Continued)

OTHER PUBLICATIONS

The Extended European Search Report dated May 24, 2019 for the related European Patent Application No. 17802511.0.
(Continued)

*Primary Examiner* — Amandeep Saini
(74) *Attorney, Agent, or Firm* — Greenblum & Bernstein, P.L.C.

(57) ABSTRACT

A skin diagnostic device includes an image acquisition unit that acquires a skin image obtained by capturing skin, an image analyzer that calculates an index value indicating a darkness level of a color of a discolored region of the skin from the obtained skin image, a threshold determination unit that determines a threshold based on the calculated index value and a size of a contrast of the skin image, and a skin diagnostic unit that performs a diagnosis on the skin by comparing the determined threshold and normalized luminance value data obtained by normalizing luminance value data of the skin image with an average luminance value of the luminance value data.

7 Claims, 19 Drawing Sheets

(51) Int. Cl.
  *A61B 5/00* (2006.01)
  *A61B 5/103* (2006.01)
(52) U.S. Cl.
  CPC ............ *A61B 5/444* (2013.01); *G06T 7/90* (2017.01); *A61B 2576/02* (2013.01); *G06T 2207/10024* (2013.01); *G06T 2207/30088* (2013.01); *G06T 2207/30201* (2013.01)
(58) Field of Classification Search
  CPC ........ G06T 2207/30201; A61B 5/0077; A61B 5/444; A61B 5/1032; A61B 2576/02
  USPC ........................................................ 382/128
  See application file for complete search history.

(56) References Cited

U.S. PATENT DOCUMENTS

| | | | | |
|---|---|---|---|---|
| 2014/0300721 | A1* | 10/2014 | Imamura | H04N 9/643 348/77 |
| 2015/0248221 | A1* | 9/2015 | Sasaki | G06T 5/008 345/173 |
| 2016/0135730 | A1 | 5/2016 | Arai et al. | |

FOREIGN PATENT DOCUMENTS

| | | |
|---|---|---|
| JP | 7-055447 A | 3/1995 |
| JP | 2004-105748 | 4/2004 |
| WO | 2014/017092 A1 | 1/2014 |
| WO | 2014/208067 | 12/2014 |

OTHER PUBLICATIONS

Gianluca Sforza et al: "Adaptive segmentation of gray areas in dermoscopy images", Medical Measurements and Applications Proceedings (MEMEA), 2011 IEEE International Workshop on IEEE, May 30, 2011 (May 30, 2011), pp. 628-631, XP031907709.

Nobuyuki Otsu, "An Automatic Threshold Selection Method Based on Discriminant and Least Squares Criteria (Partial English Translation) ", The Transactions of the Institute of Electronics and Communication Engineers of Japan, vol. J63-D, No. 4, Apr. 25, 1980 (Apr. 25, 1980), pp. 349-356.

International Search Report issued in International Patent Application No. PCT/JP2017/016128, dated Jul. 18, 2017.

\* cited by examiner

SKIN DIAGNOSTIC DEVICE AND SKIN DIAGNOSTIC METHOD

TECHNICAL FIELD

The present disclosure relates to a skin diagnostic device and a skin diagnostic method for diagnosing skin.

BACKGROUND ART

The technique described in PTL 1 makes a diagnosis on skin such as a face including extraction of a discolored region without bringing a probe or the like into contact with the skin. In the technique described in PTL 1, a density distribution is created for a skin image obtained by capturing the skin, and a discolored region such as a skin spot (melanin) is extracted by comparing a threshold with the density of each portion. At that time, the technique described in PTL 1 receives setting and change of the threshold by a manual operation.

However, an image obtained by capturing the skin (hereinafter, referred to as "skin image") is easily affected by a capturing environment. Since the density (luminance) at various places in the skin image largely changes according to the state of illumination with respect to the skin, the capturing sensitivity, the color of the skin of the ground, even if the threshold is constant, the results of the skin diagnosis differ depending on the capturing environment.

The present disclosure aims to perform a more stable skin diagnosis.

CITATION LIST

Patent Literature

PTL 1: Japanese Patent Unexamined Publication No. 2004-105748

SUMMARY OF THE INVENTION

The skin diagnostic device of the present disclosure includes an image acquisition unit that acquires a skin image obtained by capturing skin, an image analyzer that calculates an index value indicating a darkness level of the color of a discolored region of the skin from the obtained skin image, a threshold determination unit that determines a threshold based on the calculated index value and a size of a contrast of the skin image, and a skin diagnostic unit that performs a diagnosis on the skin by comparing the determined threshold and normalized luminance value data obtained by normalizing luminance value data of the skin image with an average luminance value of the luminance value data.

The skin diagnostic method of the present disclosure includes a step of acquiring a skin image obtained by capturing skin, a step of calculating an index value indicating a darkness level of the color of a discolored region of the skin from the obtained skin image, a step of determining a threshold based on the calculated index value and a size of a contrast of the skin image, and a step of performing a diagnosis on the skin by comparing the determined threshold and normalized luminance value data obtained by normalizing luminance value data of the skin image with an average luminance value of the luminance value data.

According to the present disclosure, it is possible to perform a more stable skin diagnosis.

DESCRIPTION OF EMBODIMENTS

Hereinafter, embodiments of the present disclosure will be described in detail with reference to drawings. Embodiment 1 of the present disclosure is an example of an aspect of a skin diagnostic device in the case of not controlling capturing illumination, and Embodiment 2 of the present disclosure is an example of an aspect of a skin diagnostic device in the case of controlling capturing illumination.

Embodiment 1

Outline of Device

First, the outline of the skin diagnostic device according to the present embodiment will be described.

Figure 1:
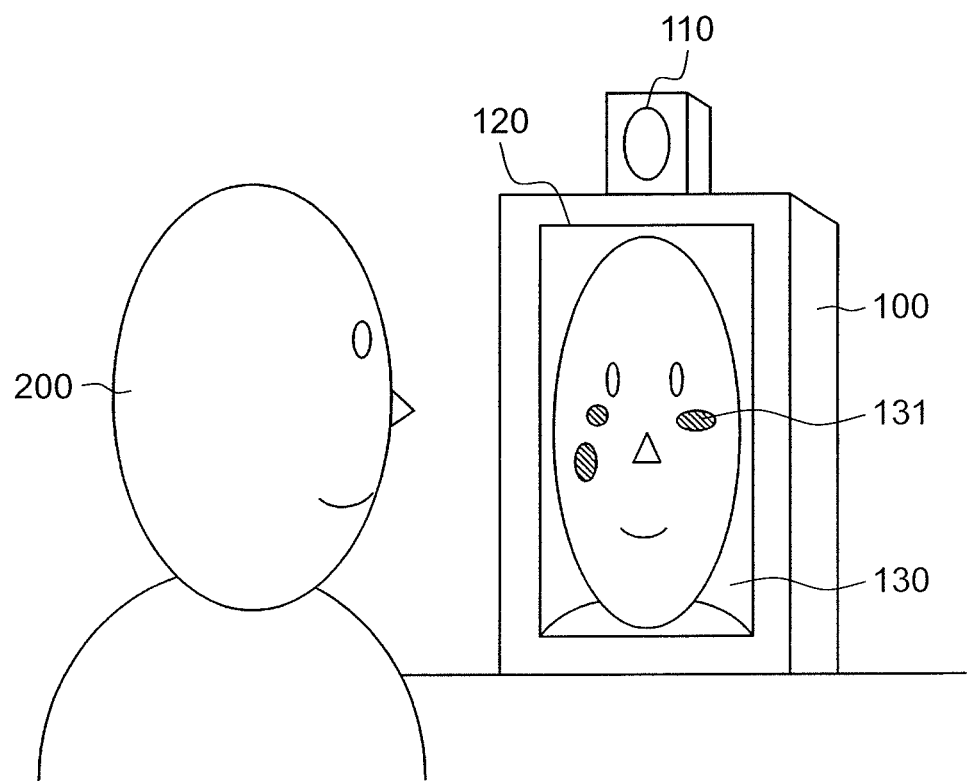
FIG. 1 is a diagram showing an example of a use state of a skin diagnostic device according to Embodiment 1 of the present disclosure.

FIG. 1 is a diagram showing an example of a use state of the skin diagnostic device according to the present embodiment.

As shown in FIG. 1, skin diagnostic device 100 is a desktop installation type device in which capturing unit 110 such as a digital camera and display 120 such as a liquid crystal display with a touch panel are disposed close to each other in the same direction. Skin diagnosis device 100 is not necessarily a device dedicated to skin diagnosis, but may be a general-purpose device such as a smartphone, a tablet type terminal, a personal computer, or the like.

In skin diagnostic device 100, the capturing unit 110 images face 200 of a user, and display 120 displays mirror image 130 in which the captured image is inverted to the left and right.

At this time, skin diagnosis device 100 performs diagnosis (hereinafter, referred to as "skin diagnosis") on the skin of face 200 by analyzing the captured image or mirror image 130 and also displays the diagnosis result. For example, skin diagnostic device 100 determines a spot portion of the skin based on mirror image 130 and displays spot image 131 indicating the determined spot portion by superimposing (mapping) spot image 131 on mirror image 130.

Figure 2:
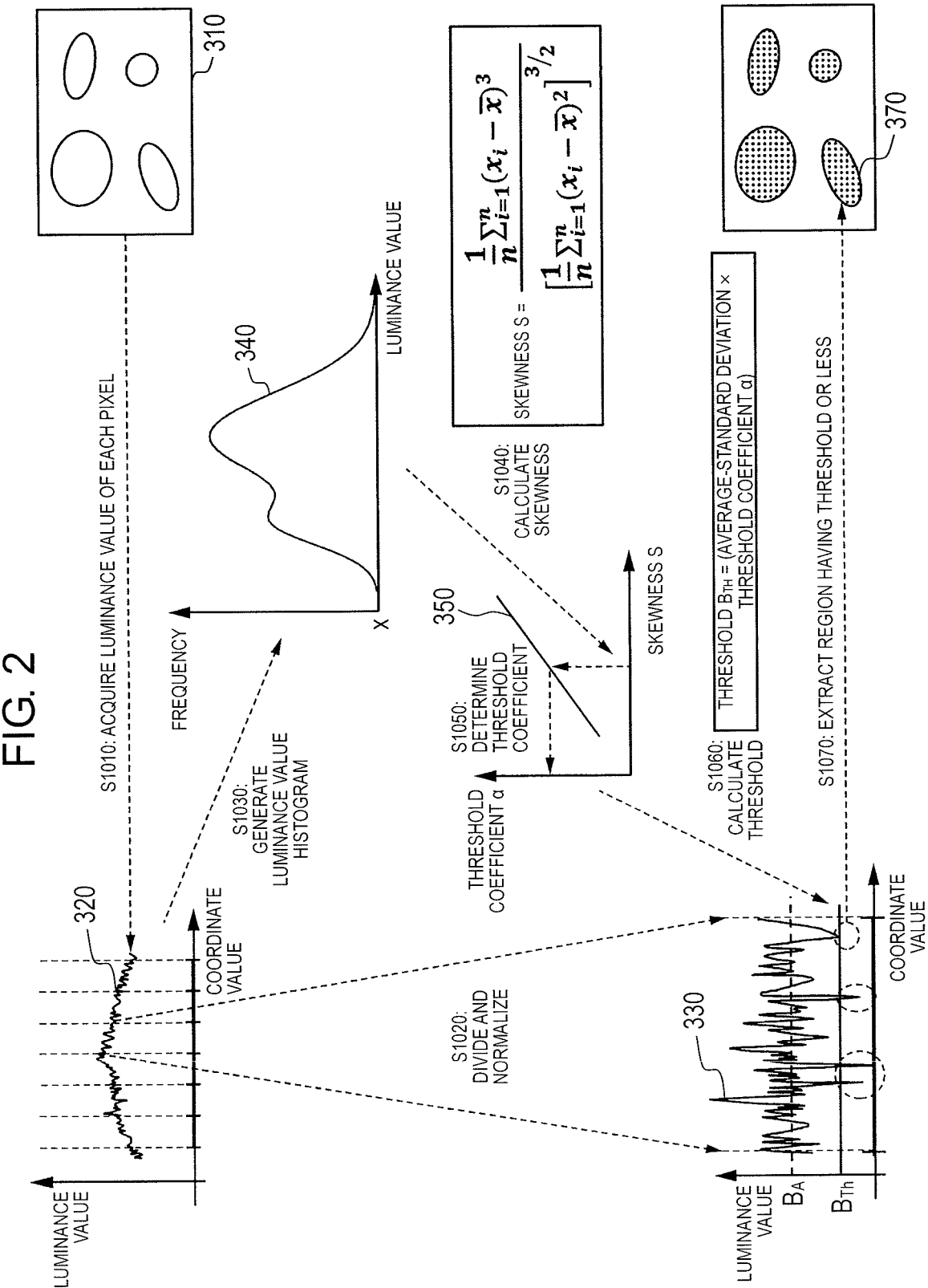
FIG. 2 is a diagram showing an example of an outline of skin diagnosis in Embodiment 1.

FIG. 2 is a diagram showing an example of an outline of skin diagnosis performed by skin diagnostic device 100.

As shown in FIG. 2, first, skin diagnostic device 100 acquires a luminance value of each pixel of region (hereinafter, referred to as "skin region" or "skin image") 310 in which the skin is reflected in mirror image 130 as luminance value data 320 associated with a coordinate value of a predetermined coordinate system (S1010). Such a coordinate system is a three- or two-dimensional coordinate system set by skin diagnostic device 100 along the skin (or skin image) of the face with reference to mirror image 130 or skin image 310.

Skin diagnostic device 100 divides luminance value data 320 obtained from skin image 310 into a plurality of blocks and performs normalization such that an average value of the luminance value data becomes a predetermined value for each block (S1020). Such normalization is performed, for example, by multiplying each luminance value by a value obtained by dividing a predetermined value by the average value of the luminance value data (including a gain, a value of 1 or more, and a value of 1 or less). In addition, the break of the block corresponds to the break of the block when, for example, skin image 310 is divided into equally spaced matrix form. As a result, normalized luminance value data (hereinafter, referred to as "normalized luminance value data") 330 is obtained for each block of skin image 310.

Skin diagnostic device 100 generates luminance value histogram 340 of skin image 310 from luminance value data 320 of skin image 310 (S1030). Luminance value histogram 340 is a histogram in which the luminance value is classified and the frequency of each luminance value in skin image 310 is frequency.

Skin diagnostic device 100 calculates skewness S indicating the degree of symmetry of the luminance distribution of luminance value histogram 340 by using, for example, the following Equation (1) (S1040).

[Equation 1]

$$S = \frac{\frac{1}{n}\sum_{i=1}^{n}(x_i - \bar{x})^3}{\left[\frac{1}{n}\sum_{i=1}^{n}(x_i - \bar{x})^2\right]^{3/2}} \quad (1)$$

Here, i is the number of each pixel of skin image 310, and n is the number of pixels (the maximum value of i) of skin image 310. In addition, $x_i$ is the normalized luminance value of the pixel of number i.

$\bar{x}$ [Equation 2]

The value of Equation 2 is an average value of the normalized luminance values of all the pixels of skin image 310.

Then, skin diagnostic device 100 determines threshold coefficient α from calculated skewness S according to predetermined conversion rule 350 (S1050). Furthermore, skin diagnostic device 100 calculates threshold $B_{Th}$ by using determined threshold coefficient α, for example, by using the following Equation (2) for each normalized luminance value data 330 (S1060).

$$B_{Th} = B_A \times \alpha \quad (2)$$

Here, $B_A$ is an average value (hereinafter, referred to as "average luminance value") of luminance values in normalized luminance value data 330, and s is a standard deviation of luminance values in normalized luminance value data 330. Since normalized luminance value data 330 is generated by normalizing with the average value of the luminance value data of an original block, average luminance value $B_A$ has a constant value.

Skin diagnostic device 100 compares calculated threshold $B_{Th}$ with the value of normalized luminance value data 330 and extracts region (coordinate value) 360 in which the value of normalized luminance value data 330 is less than threshold $B_{Th}$ as spot portion 370 (S1070).

That is, skin diagnostic device 100 calculates skewness S from the luminance value data of skin image 310, determines threshold $B_{Th}$ based on skewness S, and determines a region where a luminance value is less than threshold $B_{Th}$ as a spot region.

Significance of Using Skewness

Here, the significance of using skewness S will be described. As a comparison, first, a case where threshold $B_{Th}$ to be compared with normalized luminance value data 330 is set as a fixed value without using skewness S will be described.

Figure 3:
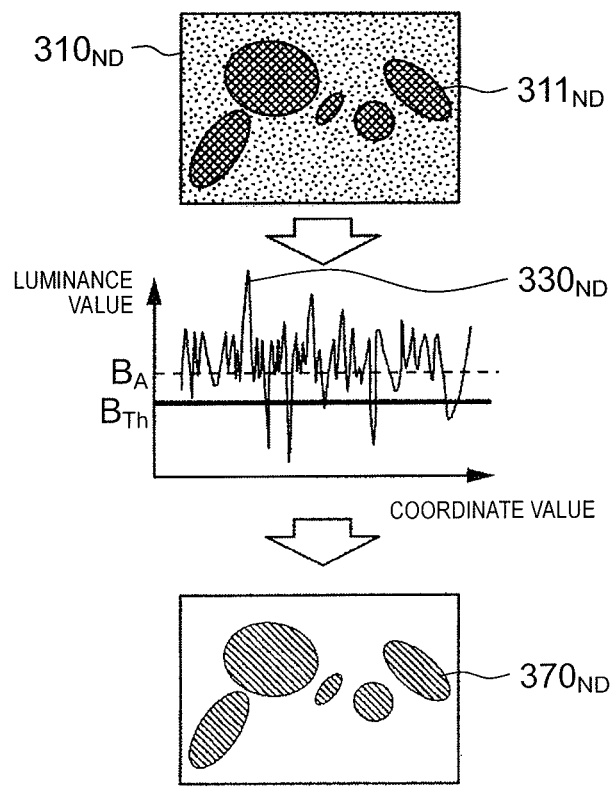
FIG. 3 is a diagram showing an example of a state of skin diagnosis for skin having dark spots in a case where a threshold is a fixed value.

FIG. 3 is a diagram showing an example of a state of skin diagnosis for a skin having dark spots in a case where threshold $B_{Th}$ is set to a fixed value. In addition, FIG. 4 is a diagram showing an example of a state of skin diagnosis for a skin having light spots in a case where the threshold is set to a fixed value.

Figure 4:
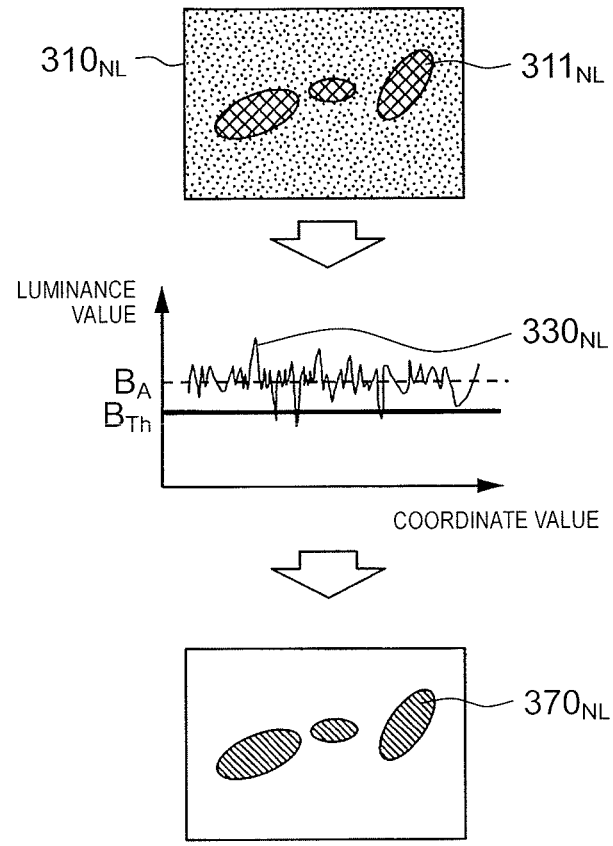
FIG. 4 is a diagram showing an example of a state of skin diagnosis for skin having light spots in a case where the threshold is a fixed value.

In FIGS. 3 and 4, skin images $310_{ND}$ and $310_{NL}$ are images including a skin image having dark spot $311_{ND}$ and a skin image having light spot $311_{NL}$ captured in a capturing environment (hereinafter, referred to as "reference environment") as a reference, which are shown close to a visual impression.

As shown in FIGS. 3 and 4, the contrast (fluctuation width of normalized luminance value data $330_{NL}$) of skin image $310_{NL}$ having light spot $311_{NL}$ is smaller than the contrast (fluctuation width of normalized luminance value data $330_{ND}$) of skin image $310_{ND}$ having dark spot $311_{ND}$.

Here, in both skin images $310_{ND}$ and $310_{NL}$, it is assume that threshold $B_{Th}$ of a fixed value is determined based on experiments and the like such that spot 311 with the darkness visually recognized is detected as completely as possible without an error. In this case, spot portions $370_{ND}$ and $370_{NL}$ extracted by the comparison between normalized luminance value data $330_{ND}$ and $330_{NL}$ of skin images $310_{ND}$ and $310_{NL}$ and threshold $B_{Th}$ substantially coincide with the regions of spots $311_{ND}$ and $311_{NL}$ which are visually recognized. That is, spots are detected as good as possible.

However, in an environment brighter than the reference environment, the contrast between the spot 311 and the surrounding skin portions increases, and the detection result of the spot 311 changes.

Figure 5:
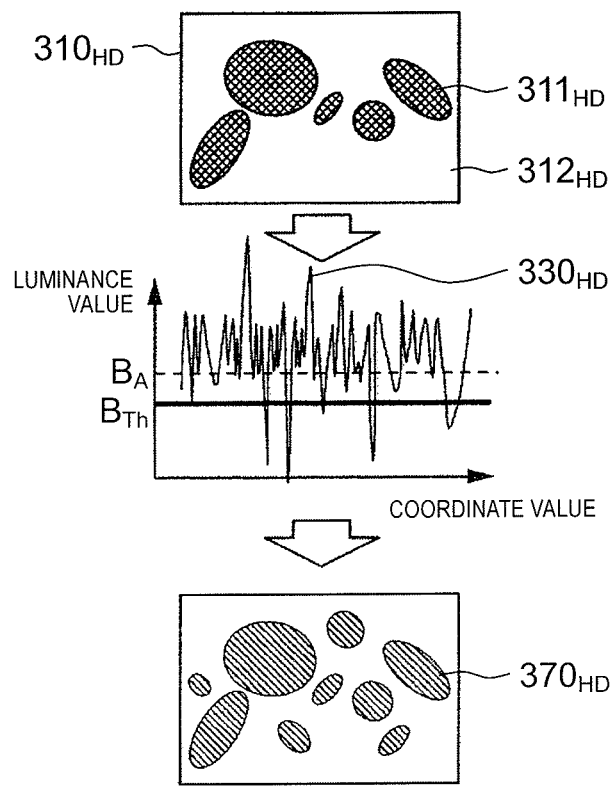
FIG. 5 is a diagram showing an example of a state of skin diagnosis for the skin having dark spots in a case where the threshold is a fixed value and an environment is bright.
Figure 6:
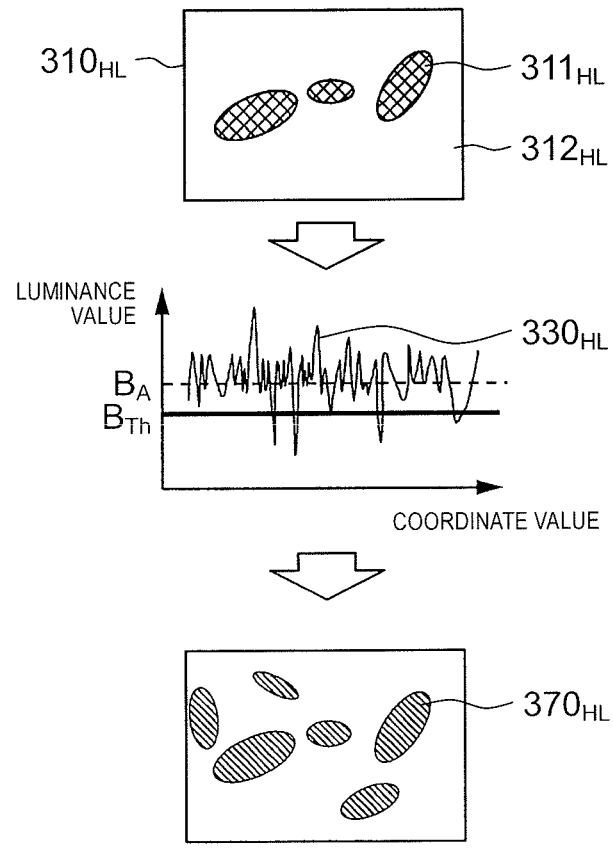
FIG. 6 is a diagram showing an example of a state of skin diagnosis for the skin having light spots in a case where the threshold is a fixed value and an environment is bright.

FIGS. 5 and 6 are diagrams showing examples of skin diagnosis in an environment that is brighter than the reference environment (high illuminance) and correspond to FIGS. 3 and 4.

In the case of a bright environment, as shown in FIGS. 5 and 6, skin images $310_{HD}$ and $310_{HL}$ generally have higher luminance than skin images $310_{ND}$ and $310_{NL}$ shown in FIGS. 3 and 4. However, since spots $311_{HD}$ and $311_{HL}$ are darker in color than the surrounding skin, and the relative luminance change thereof becomes smaller. Therefore, the luminance difference between spots $311_{HD}$ and $311_{HL}$ and the other skin portions $312_{HD}$ and $312_{HL}$ increases, and the fluctuation width (contrast) of normalized luminance value data $330_{HD}$ and $330_{HL}$ also increases.

As a result, as shown in FIGS. 5 and 6, if the same fixed threshold $B_{Th}$ as in the reference environment is used, the number of the regions where the luminance value is less than threshold $B_{Th}$ increases, and more regions are extracted as spot portions $370_{HD}$ and $370_{HL}$. That is, spots are detected excessively.

Therefore, threshold $B_{Th}$ is determined by using, for example, the following Equation (3) so that the detection of spots is more suppressed as the fluctuation width of normalized luminance value data 330 is larger.

$$B_{Th} = B_A \cdot s \times \beta \quad (3)$$

Here, β is a threshold coefficient, which is a value such that spots are detected as good as possible in skin images $310_{ND}$ and $310_{HD}$ of skin having dark spots and is a fixed value obtained by experiments or the like.

Figure 7:
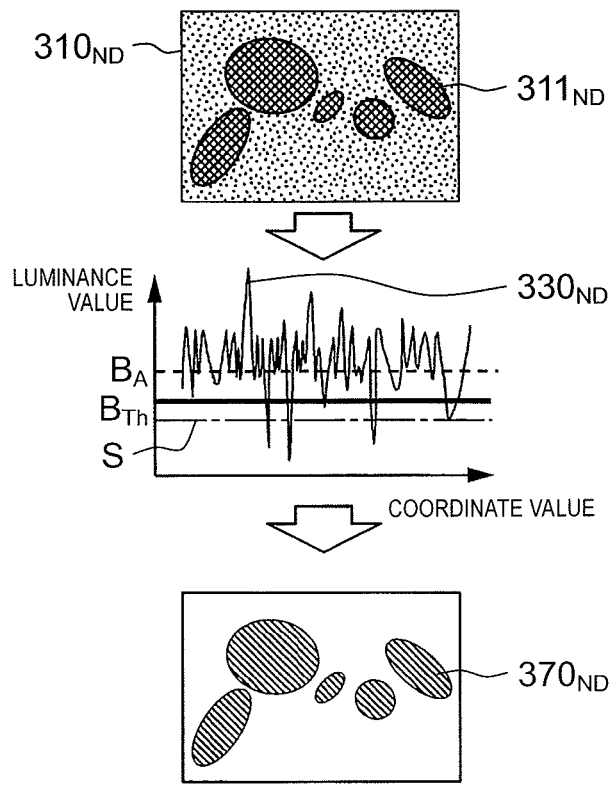
FIG. 7 is a diagram showing an example of a state of skin diagnosis for the skin having dark spots in a case where the threshold is determined according to a contrast.
Figure 8:
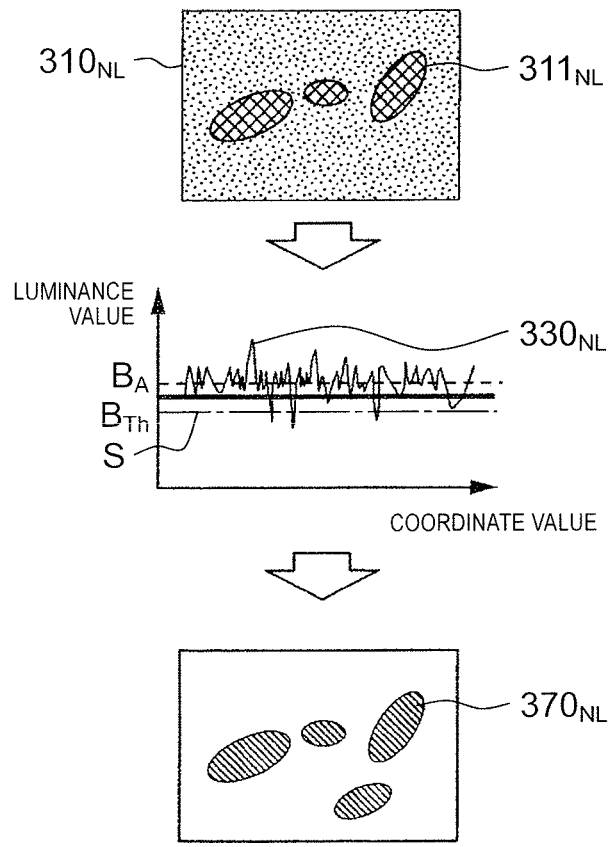
FIG. 8 is a diagram showing an example of a state of skin diagnosis for the skin having light spots in a case where the threshold is determined according to the contrast.

FIGS. 7 and 8 are diagrams showing examples of the state of skin diagnosis in the case where threshold $B_{Th}$ is determined by using the above-described Equation (3) and correspond to FIGS. 3 and 4.

In the above-described Equation (3), threshold $B_{Th}$ decreases as standard deviation s of normalized luminance value data 330 increases, and it is difficult for spots to be detected. Therefore, in skin image $310_{ND}$ of dark spot $311_{ND}$, a desired amount of spot portion $370_{ND}$ is extracted.

However, since standard deviation s of normalized luminance value data $330_{NL}$ of skin image $310_{NL}$ of light spot $311_{NL}$ is smaller than standard deviation s of normalized luminance value data $330_{ND}$ of skin image $310_{ND}$ of dark spot $311_{ND}$, threshold $B_{Th}$ becomes relatively high.

As a result, as shown in FIGS. 7 and 8, from dark spot $311_{ND}$, a good amount of spot portion $370_{ND}$ is extracted, whereas slightly larger spot portion $370_{NL}$ is extracted from light spot $311_{NL}$. That is, light spot $311_{NL}$ is detected somewhat excessively. This tendency is the same also in a bright environment.

Figure 9:
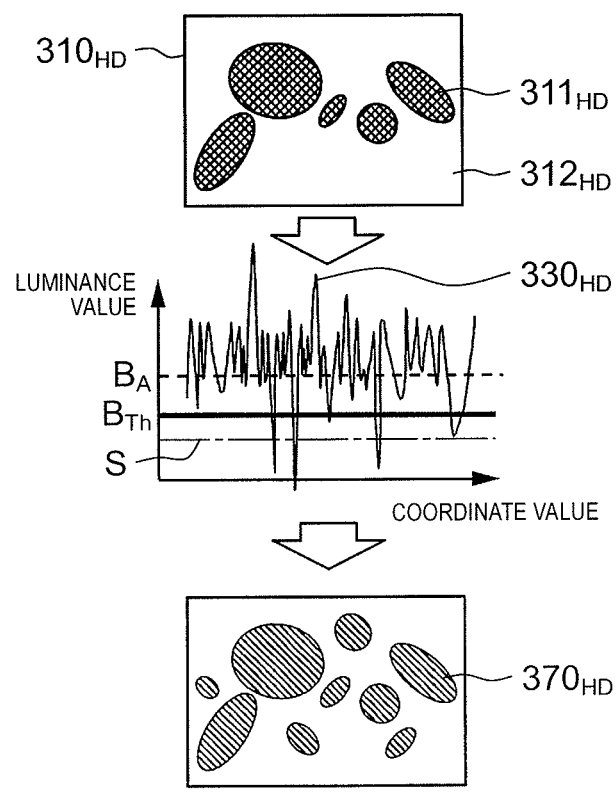
FIG. 9 is a diagram showing an example of a state of skin diagnosis for the skin having dark spots in a case where the environment is bright with the threshold being variable according to the contrast.
Figure 10:
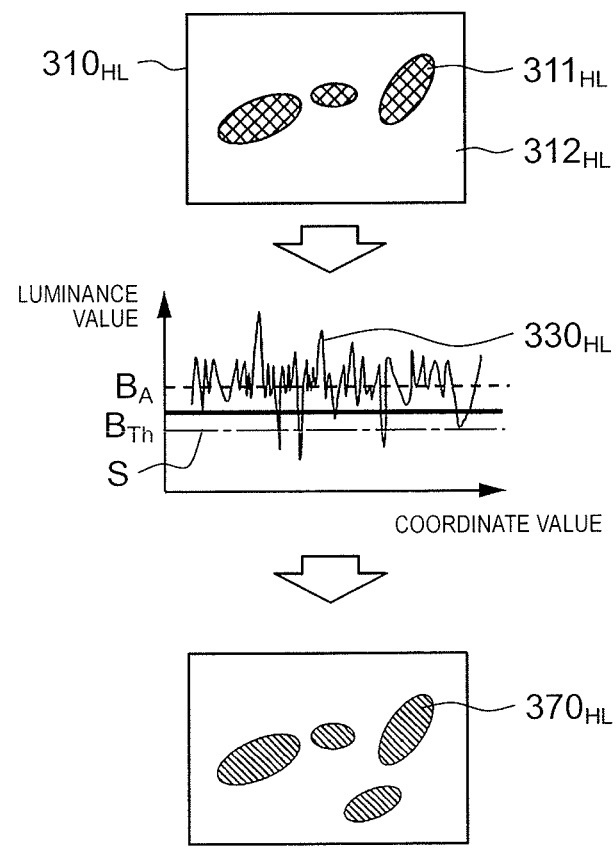
FIG. 10 is a diagram showing an example of a state of skin diagnosis for the skin having light spots in a case where the environment is bright with the threshold being variable according to the contrast.

FIGS. 9 and 10 are diagrams showing examples of the state of skin diagnosis in a case where threshold $B_{Th}$ is determined by using the above-described Equation (3) in an environment brighter than the reference environment (high illuminance) and correspond to FIGS. 5 and 6. As shown in FIG. 10, even in a case where the illumination is bright, light spot $311_{HL}$ is detected somewhat excessively.

Therefore, skin diagnostic device 100 according to the present embodiment reduces excessive detection of light spot $311_{HL}$ by determining a threshold coefficient (α in Equation (2)) by which standard deviation s is multiplied so that the threshold coefficient becomes lower as spot 311 is lighter.

However, how to determine a darkness level of the color of spot 311 is a problem. Therefore, as described with reference to FIG. 2, skin diagnostic device 100 according to the present embodiment calculates skewness S for each normalized luminance value data 330 and determines threshold coefficient α as a variable based on the calculation result. As a result, skin diagnostic device 100 reduces the difference in extraction accuracy caused by the darkness of the color of spot 311.

Here, the relationship between the darkness of the color of spot 311 and skewness S will be described.

Figure 11:
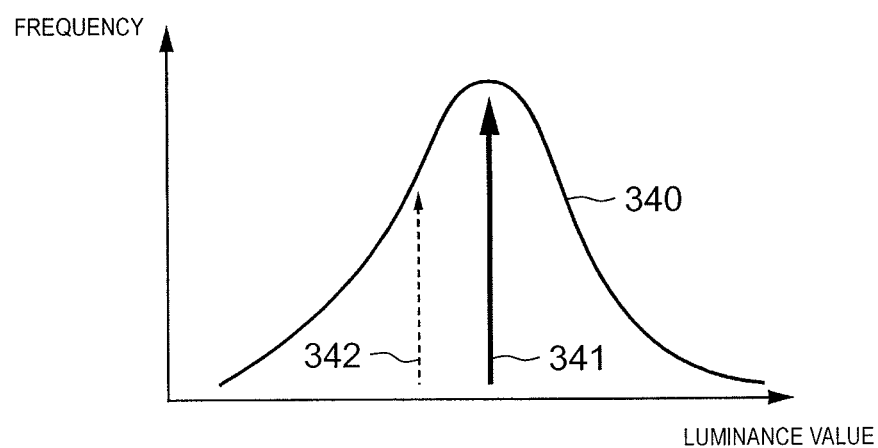
FIG. 11 is a diagram showing an example of a luminance value histogram of the skin having light spots.

FIG. 11 is a diagram showing an example of luminance value histogram 340 in a case where spot 311 is light.

Figure 12:
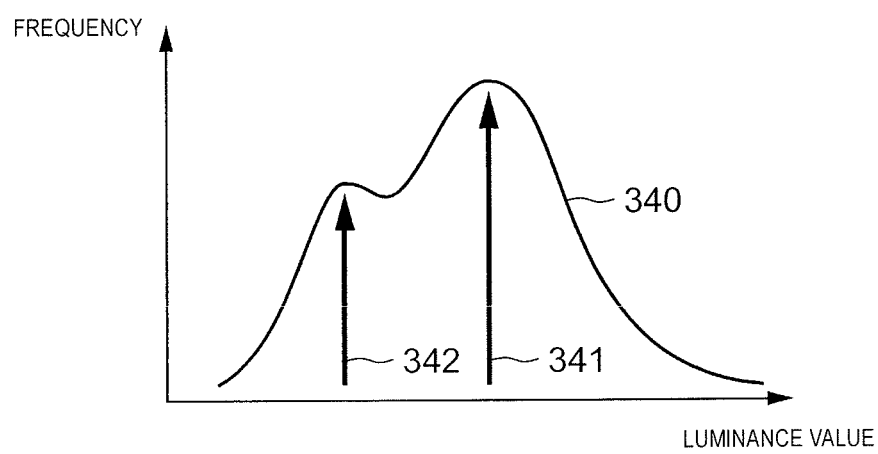
FIG. 12 is a diagram showing an example of a luminance value histogram of the skin having dark spots.

FIG. 12 is a diagram showing an example of luminance value histogram 340 in a case where spot 311 is dark.

As shown in FIGS. 11 and 12, luminance value histogram 340 has a mountain-like shape having a vertex in luminance value component 341 of the portion without skin spot 311. In a case where spots 311 are small, it is assumed that luminance value histogram 340 of skin image 310 has a shape that is symmetrical with respect to a luminance value axis and is close to a normal distribution (for example, see Tomohiro MASHITA, Yasuhiro MUKAIGAWA, and Yasushi YAGI, "Representation of anisotropic scattering and non-uniformity of skin by multilayer subsurface scattering model", image recognition and understanding symposium (MIRU 2009), July 2009, IS2-53: 1216-1222).

However, due to the presence of the spot 311, such symmetry is lost. As spot 311 is darker, the influence of luminance value component 342 of the spot portion becomes stronger, and luminance value histogram 340 has components whose luminance values are lower than a vertex increase. As a result, as spot 311 is darker, the symmetry of luminance value histogram 340 is more greatly reduced.

On the other hand, skewness S represented by the above-described Equation (1) is an index value indicating the degree of symmetry (symmetry of luminance distribution) in the luminance value axis direction of luminance value histogram 340. Skewness S takes zero or a negative value, approaches zero as the symmetry increases (as the asymmetry decreases), and decreases (the absolute value of the negative value increases) as the symmetry decreases (as the asymmetry increases).

Therefore, it may be said that spot 311 in the corresponding region is darker as skewness S is lower. Skin diagnostic device 100 determines threshold coefficient α so that threshold coefficient α becomes a higher value as skewness S is higher by using the correspondence relationship.

For example, skin diagnostic device 100 calculates skewness S for each of normalized luminance value data 330 and converts skewness S into threshold function α according to conversion rule 350 (see FIG. 2) which is a regression equation of a linear function of skewness S-threshold function α. Conversion rule 350 is, for example, a content in which a value obtained by adding a first positive value to skewness S and then multiplying the first positive value by a second positive value is set as threshold coefficient α. Then, skin diagnostic device 100 calculates threshold $B_{Th}$ from threshold function α by using the above-described Equation (2).

Figure 13:
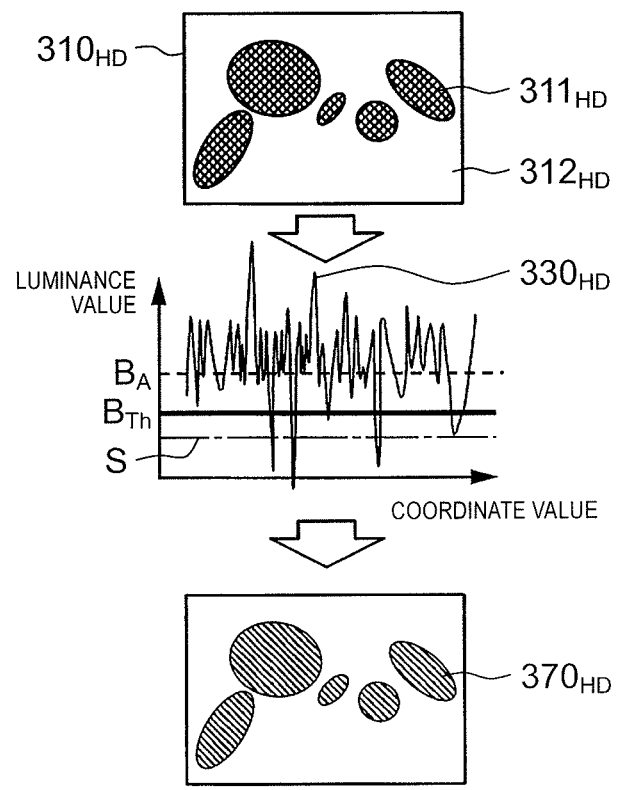
FIG. 13 is a diagram showing an example of a state of skin diagnosis for the skin having dark spots in a case where the threshold is determined according to the contrast and a skewness in Embodiment 1.
Figure 14:
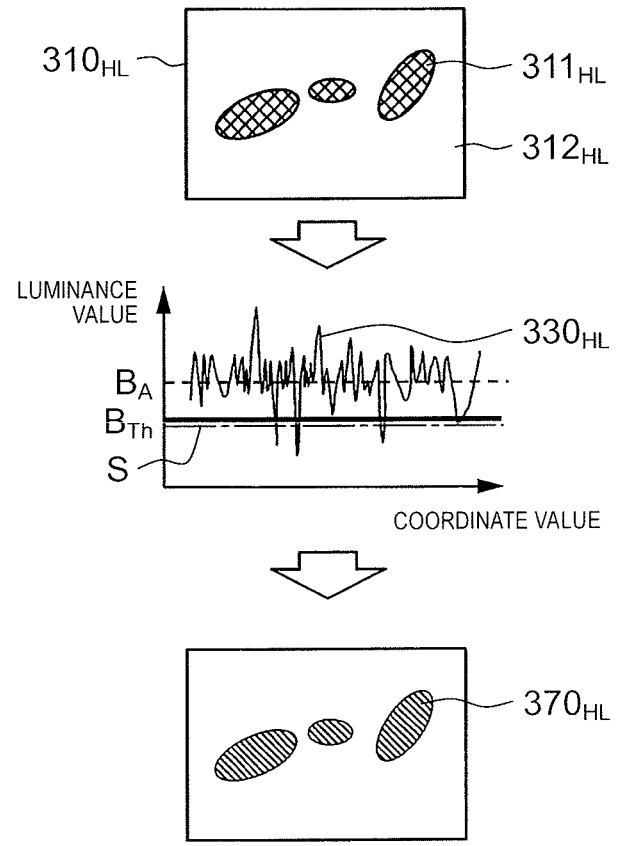
FIG. 14 is a diagram showing an example of a state of skin diagnosis for the skin having light spots in a case where the threshold is determined according to the contrast and the skewness in Embodiment 1.

FIGS. 13 and 14 are diagrams showing examples of the state of skin diagnosis in a case where threshold $B_{Th}$ is determined according to the skewness and correspond to FIGS. 9 and 10.

In the case of light spot $311_{HL}$, since skewness S is high (close to zero), the value of threshold function α becomes larger, and the second term (s×α) on the right side of Equation (2) subtracted from average luminance value $B_A$ also becomes larger. As a result, as shown in FIG. 14, calculated threshold $B_{Th}$ becomes smaller than $B_{Th}$ used in FIG. 10, and a good amount of spot portion $370_{HL}$ is extracted by appropriately setting a regression equation.

In this manner, skin diagnostic device 100 may extract a good amount of spots 311 having various darkness by adjusting threshold $B_{Th}$ based on skewness S while suppressing the influence by the capturing environment.

Configuration of Device

Next, the configuration of skin diagnostic device 100 will be described.

Figure 15:
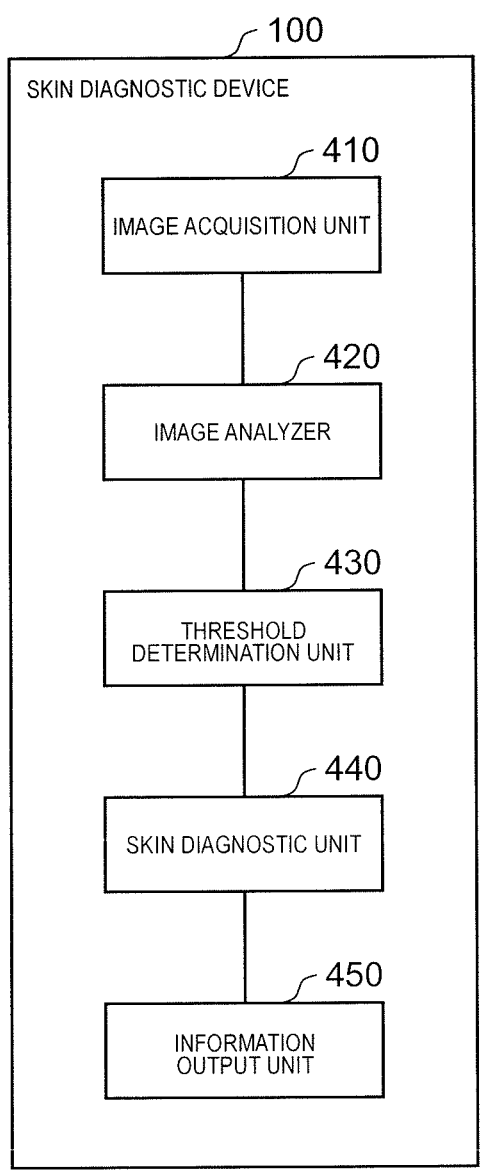
FIG. 15 is a block diagram showing an example of a configuration of the skin diagnostic device according to Embodiment 1.

FIG. 15 is a block diagram showing an example of the configuration of skin diagnostic device 100.

In FIG. 15, skin diagnostic device 100 includes image acquisition unit 410, image analyzer 420, threshold determination unit 430, skin diagnostic unit 440, and information output unit 450.

Image acquisition unit 410 acquires skin image 310 obtained by capturing the skin and outputs obtained skin image 310 to image analyzer 420. Image acquisition unit 410 includes, for example, above-described imaging unit 110 (see FIG. 1), receives a user operation or the like on the above-described touch panel, captures face 200 of the user, inverts the captured image including skin image 310 of face 200 to the left and right, and outputs mirror image 130 to image analyzer 420.

Image analyzer 420 extracts the face region and the facial portions such as eyes, a nose, a mouth, and the like and extracts the region excluding the facial portions from the face region as skin image 310, for example, from mirror image 130 by a known image analysis technique such as a pattern recognition technique or a color analysis technique. In addition, image analyzer 420 calculates skewness S of skin image 310 by using, for example, the above-described Equation (1) based on extracted skin image 310.

Then, image analyzer 420 outputs mirror image 130, extracted skin image 310 (or information indicating the range of the skin region in mirror image 130), and calculated skewness S to threshold determination unit 430. Calculation of skewness S may be performed in threshold determination unit 430 in the subsequent stage.

Threshold determination unit 430 determines threshold coefficient α based on skewness S according to predetermined conversion rule 350 (see FIG. 2) and generates normalized luminance value data 330 for each block from skin image 310 to calculate standard deviation s of each normalized luminance value data 330. Then, based on the determined threshold coefficient α and calculated standard deviation s, threshold determination unit 430 calculates threshold $B_{Th}$ by using, for example, the above-described Equation (2).

Then, threshold determination unit 430 outputs mirror image 130, normalized luminance value data 330 of each block, and calculated threshold $B_{Th}$ to skin diagnostic unit 440. The generation of normalized luminance value data 330 for each block and the calculation of standard deviation s may be performed in image analyzer 420.

Skin diagnostic unit 440 compares each value of normalized luminance value data 330 with threshold $B_{Th}$ for each block of skin image 310 and determines that the portion where the luminance value is less than threshold $B_{Th}$ is a spot portion. Then, skin diagnostic unit 440 outputs mirror image 130 and information (hereinafter, referred to as "spot region information") indicating the region of the spot portion in mirror image 130 to information output unit 450.

Skin diagnostic unit 440 may determine that the region is a spot portion on the condition that a series of regions whose luminance values are less than threshold $B_{Th}$ is equal to or larger than a predetermined area (a predetermined number of pixels or more). As a result, it is possible to detect spots in a case where the influence of image noise being reduced.

Based on the spot region information, information output unit 450 generates spot image 131 indicating a spot portion and superimposes and displays spot image 131 on the skin region (skin image 310) of mirror image 130 (see FIG. 1). Information output unit 450 includes, for example, above-described display 120 (see FIG. 1).

Skin diagnostic device 100 includes, for example, a central processing unit (CPU), a storage medium such as a read only memory (ROM) storing a control program, and a work memory such as a random access memory (RAM). In this case, the functions of the above-described units are realized by the CPU executing the control program.

With such a configuration, skin diagnostic device 100 may extract spot portion 370 by adjusting threshold $B_{Th}$ to be compared with the luminance value of each portion of skin image 310 according to skewness S of skin image 310.

Operation of Device

Next, the operation of skin diagnostic device 100 will be described.

Figure 16:
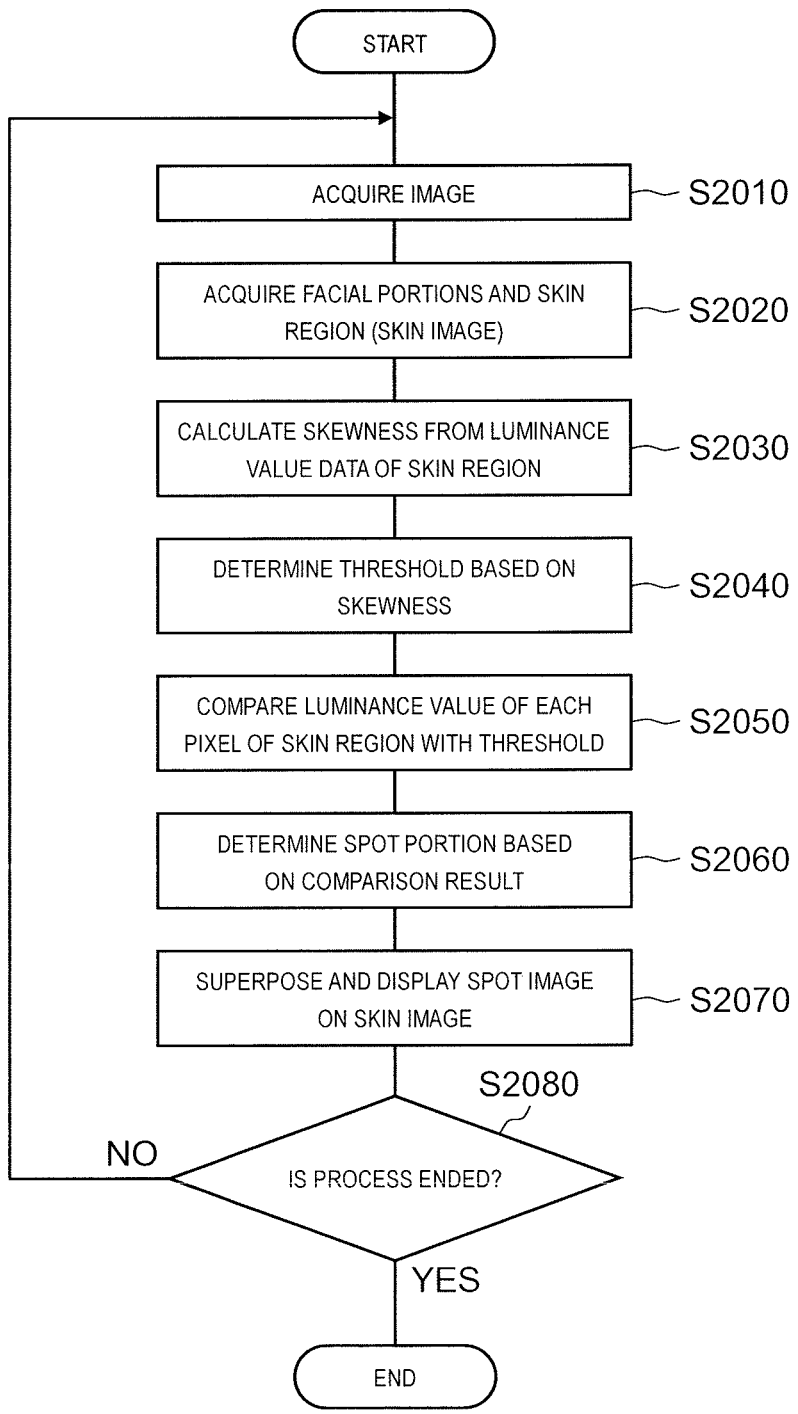
FIG. 16 is a flowchart showing an example of an operation of the skin diagnostic device according to Embodiment 1.

FIG. 16 is a flowchart showing an example of the operation of skin diagnostic device 100.

In step S2010, image acquisition unit 410 acquires mirror image 130 obtained by inverting the captured image to the left and right.

In step S2020, image analyzer 420 acquires facial portions and a skin region (skin image 310) from mirror image 130.

In step S2030, image analyzer 420 calculates skewness S from the luminance value data of skin region (skin image 310). The skin region (hereinafter, referred to as "skewness calculation target region") used to calculate skewness may be common (for example, all skin regions) for a plurality of blocks or may be different for each block. However, it is desirable for image analyzer 420 to use an image range including a block and larger than the block in skin image 310 as a skewness calculation target region for the block.

Figure 17:
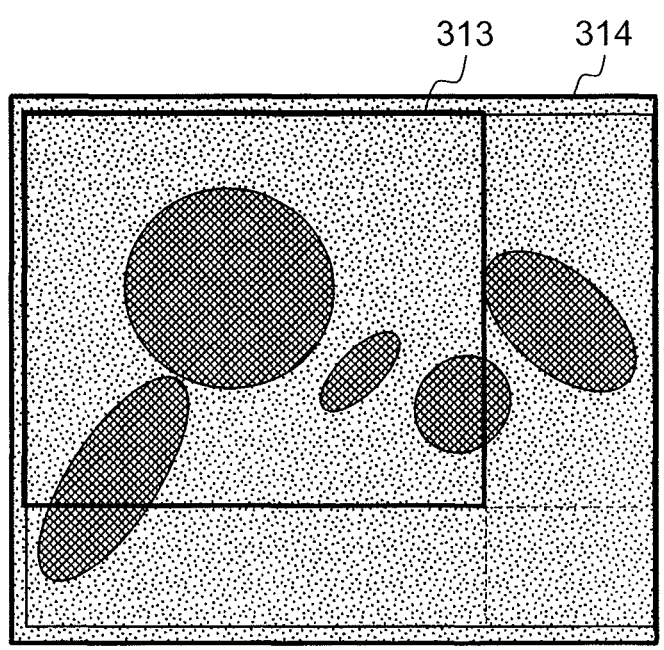
FIG. 17 is a diagram showing an example of a relationship between a block and a skewness calculation target region in Embodiment 1.

FIG. 17 is a diagram showing an example of the relationship between the block and the skewness calculation target region for the block.

As shown in FIG. 17, image analyzer 420 sets skewness calculation target region 314 such that skewness calculation target region 314 includes block 313 and is larger than block 313.

In step S2040 of FIG. 16, threshold determination unit 430 determines threshold $B_{Th}$ based on calculated skewness S according to conversion rule 350 and Equation (2). As described above, threshold $B_{Th}$ becomes a lower value as skewness S is higher (as spot 311 is lighter) and the contrast of skin image 310 is larger (as the capturing environment is brighter).

In step S2050, skin diagnostic unit 440 compares the luminance value of each pixel of the skin region (skin image 310) with determined threshold $B_{Th}$ for each block.

In step S2060, skin diagnostic unit 440 determines a spot portion of skin image 310 (mirror image 130) based on the result of the comparison.

In step S2070, information output unit 450 superimposes and displays a spot image indicating a spot portion on skin image 310 (mirror image 130).

In step S2080, image acquisition unit 410 determines whether or not the end of the process is instructed by a user operation or the like. In a case where the end of the process is not instructed (S2080: NO), image acquisition unit 410 returns the process to step S2010. In addition, in a case where the end of the process is instructed (S2080: YES), image acquisition unit 410 ends the series of processes.

When mirror image 130 is time-series image data, that is, video (moving image), skin diagnostic unit 440 may convert the region indicating the spot portion into the value of the relative coordinate system with reference to the facial portions or facial feature points (points that will be features of the face such as the corner of the eyes and mouth) and hold the region. In this case, for example, skin diagnostic device 100 omits steps S2030 to S2070 in the second and subsequent processes and sequentially moves and deforms the spot images in accordance with the change in the position, direction, and facial expression of face 200 of the user.

With such an operation, skin diagnostic device 100 may extract spot portion 370 by adjusting threshold $B_{Th}$ to be compared with the luminance value of each portion of skin image 310 according to skewness S of skin image 310.

Effect of Present Embodiment

As described above, skin diagnostic device 100 according to the present embodiment includes image acquisition unit 410 that acquires skin image 310 obtained by capturing skin and image analyzer 420 that calculates an index value (skewness S) indicating of a darkness level of a color of a discolored region of the skin from obtained skin image 310. In addition, skin diagnostic device 100 includes threshold determination unit 430 that determines threshold $B_{Th}$ based on the calculated index value (skewness S) and the magnitude (standard deviation s) of contrast of skin image 310. Then, skin diagnostic device 100 includes skin diagnostic unit 440 that performs diagnosis on the skin by comparing determined threshold $B_{Th}$ with normalized luminance value data 330 obtained by normalizing luminance value data 320 of skin image 310 with the average luminance value of luminance value data 320.

With such a configuration, it is possible to perform a more stable skin diagnosis.

Modification Example of Present Embodiment

The index value indicating the darkness level of the color of the discolored region of the skin and the magnitude of the contrast of the skin image calculated by image analyzer 420 are not limited to skewness S and standard deviation s described above. For example, as an index value indicating the darkness level of the color of the discolored region of the skin, a value obtained by subtracting the number of pixels having a luminance value equal to or less than the average luminance value from the number of pixels having the minimum value of the pixel value of the skin image, the difference between the average value and the minimum value of the pixel values of the skin image, and a luminance value higher than the average luminance value may be adopted. In addition, as the magnitude of the contrast of the skin image, the difference between the maximum value and the minimum value of the pixel value of the skin image may be adopted.

The method of determining threshold $B_{Th}$ to be compared with the normalized luminance value data based on the index value indicating the darkness level of the color and the magnitude of the contrast is not limited to the above example. For example, threshold determination unit 430 may determine threshold $B_{Th}$ using the following Equation (4).

$$B_{Th} = \alpha \times (\text{index value indicating a darkness level of the color}) + \beta \times (\text{magnitude of the contrast}) \quad (4)$$

Coefficients $\alpha$ and $\beta$ are values determined by using a known learning method using, for example, a skin image and a set of images obtained by labeling regions determined as spots by a subjective evaluation or the like in the skin image.

The unit of the image region from which a luminance value is obtained is not necessarily a pixel but may be a small area having a constant area which is composed of a plurality of pixels. For example, the unit of the image region from which a luminance value is obtained may be a small block obtained by further dividing the above-described block into a matrix. In this case, as the luminance value of the small block, for example, the average value of the luminance values of each pixel in the small block may be adopted.

The content of the skin diagnosis and the method of presenting the diagnosis result are not limited to the above example. For example, skin diagnostic unit 440 may calculate a skin state index value indicating the transparency of the skin based on the detected amount and the darkness of the spot portion and create a skin index value map indicating the distribution of the calculated values. Then, information output unit 450 may superimpose and display an image indicating the generated index value map on skin image 310. In addition, information output unit 450 may display the evaluation result of the entire face with 100 full points or the like. Further, information output unit 450 may present various kinds of information such as skin care information, cosmetics information, eating habit improvement information, and the like based on the skin diagnosis result (see, for example, International Publication No. 2014/208067).

Skin diagnostic device 100 may internally store various data including the diagnosis result or may transmit and accumulate the data to an external database to manage the log of the stored/accumulated information. Furthermore, skin diagnostic device 100 may compare the latest data with the past data to present the comparison result.

The discolored region to be detected is not limited to spots and may be a region where the lightness is lower than a predetermined level than the surroundings in the region of the skin such as black moles, rashes, and the like. Furthermore, the discolored region to be detected is not necessarily a discolored region that is easy to be visually recognized and may include, for example, a potentially discolored region existing at the back of the skin. In addition, the "luminance value" may be replaced with other various pixel values such as R value of RGB. Furthermore, depending on the contents of the skin diagnosis, skin diagnostic device 100 may acquire a skin image by using a polarizing filter, a wavelength filter, or the like.

A part of the configuration of skin diagnostic device 100 may be physically separated from other parts of the configuration of the device. In this case, it is necessary for each of these separated parts to have a communicator for communicating with each other.

Embodiment 2

In each figure, the same reference numerals/step numbers are assigned to the same parts as those in Embodiment 1, and the description thereof is appropriately omitted.

Outline of Device

First, the outline of the skin diagnostic device according to the present embodiment will be described.

Figure 18:
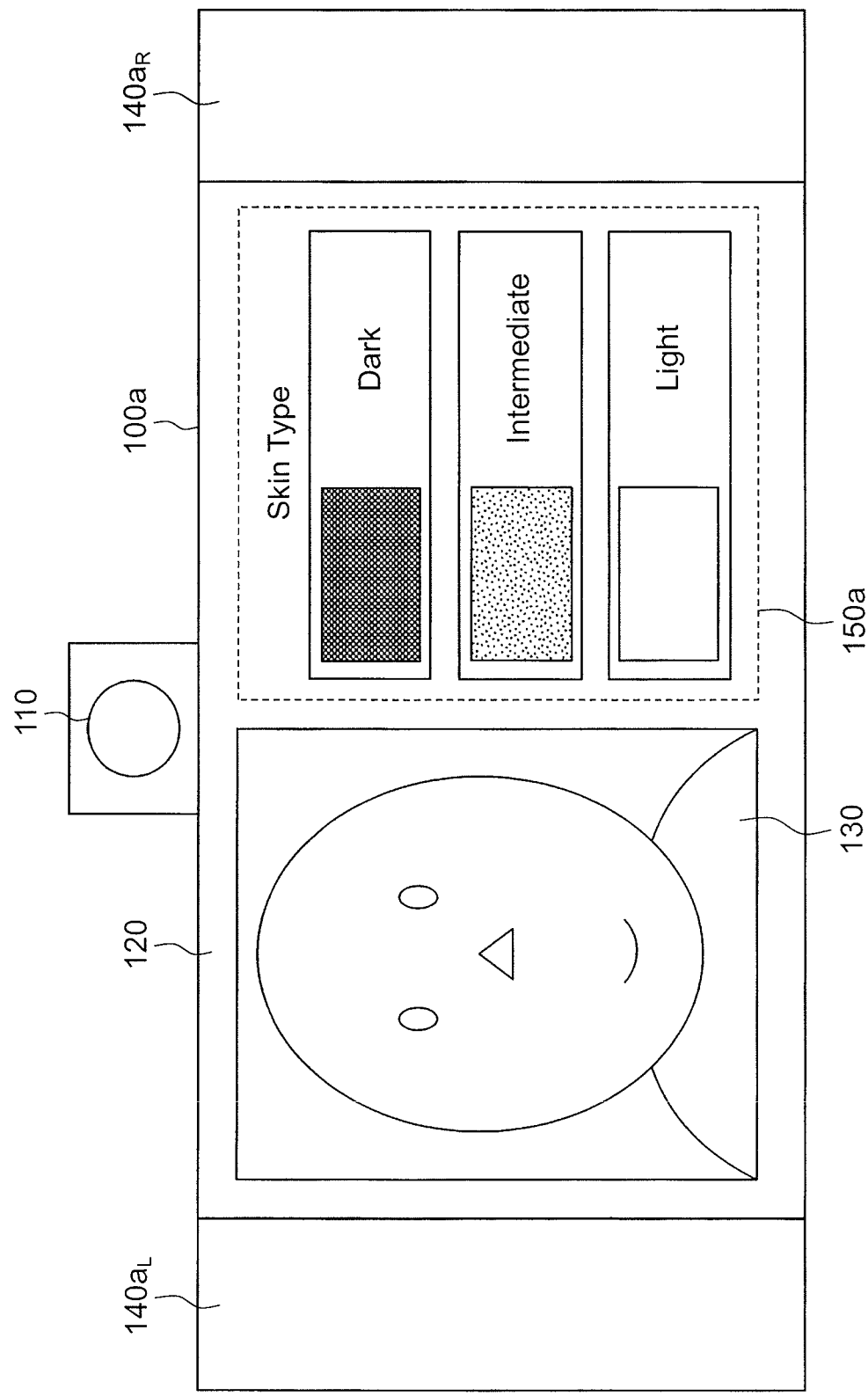
FIG. 18 is a diagram showing an example of an appearance of a skin diagnostic device according to Embodiment 2 of the present disclosure.
Figure 19:
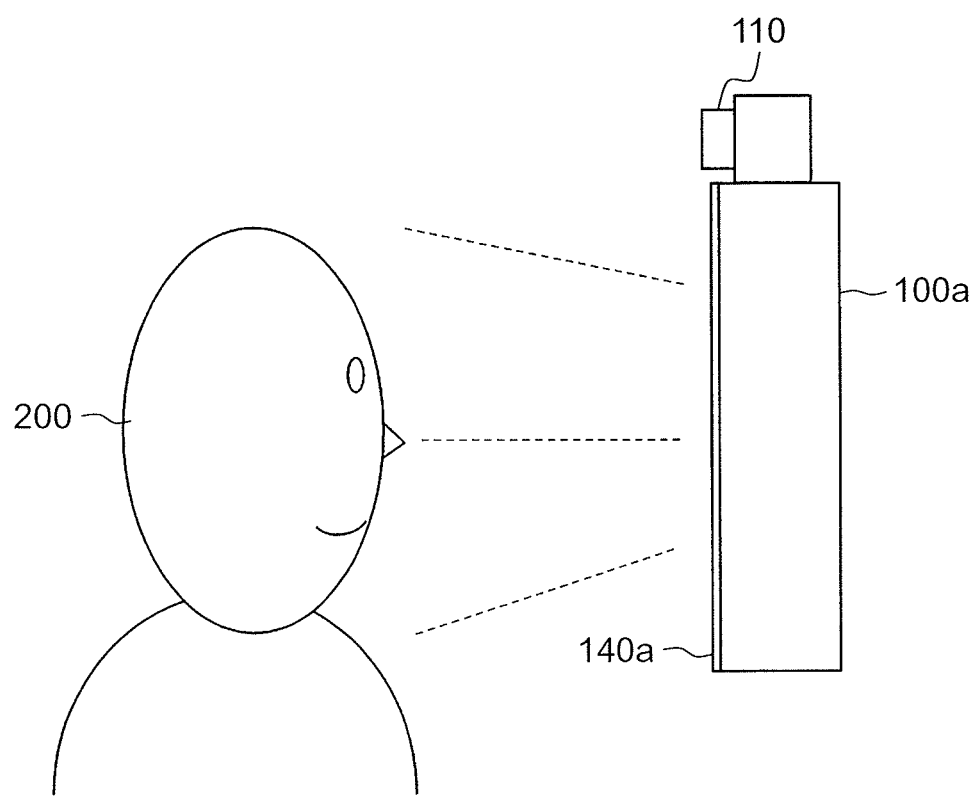
FIG. 19 is a diagram showing an example of a use state of the skin diagnostic device according to Embodiment 2.

FIG. 18 is a diagram showing an example of the external appearance of the skin diagnostic device according to the present embodiment. In addition, FIG. 19 is a diagram showing an example of a use state of the skin diagnostic device according to the present embodiment.

As shown in FIG. 18, in skin diagnostic device 100a according to the present embodiment, illuminators 140a_R and 140a_L (hereinafter, referred to as "illuminator 140a" as appropriate) are disposed on the left and right sides of display 120. Illuminator 140a illuminates face 200 of the user who is the subject of the skin diagnosis at the timing when capturing unit 110 captures an image. As will be described later, illuminator 140a may adjust an output.

Skin diagnostic device 100a displays not only mirror image 130 but also skin color type selection screen 150a on display 120. Skin color type selection screen 150a is a user interface for selecting the skin color type of the user displayed in mirror image 130 and displays three kinds of skin color types of "dark" (Dark), "intermediate" (Intermediate), and "bright" (Light) are displayed as options.

For example, skin diagnostic device 100a acquires the skin color type of face 200 of the user via skin color type selection screen 150a and changes the light amount of illuminator 140a and conversion rule 350 when determining threshold $B_{Th}$ from skewness S according to the obtained skin color type.

Configuration of Device

Next, the configuration of skin diagnostic device 100a will be described.

Figure 20:
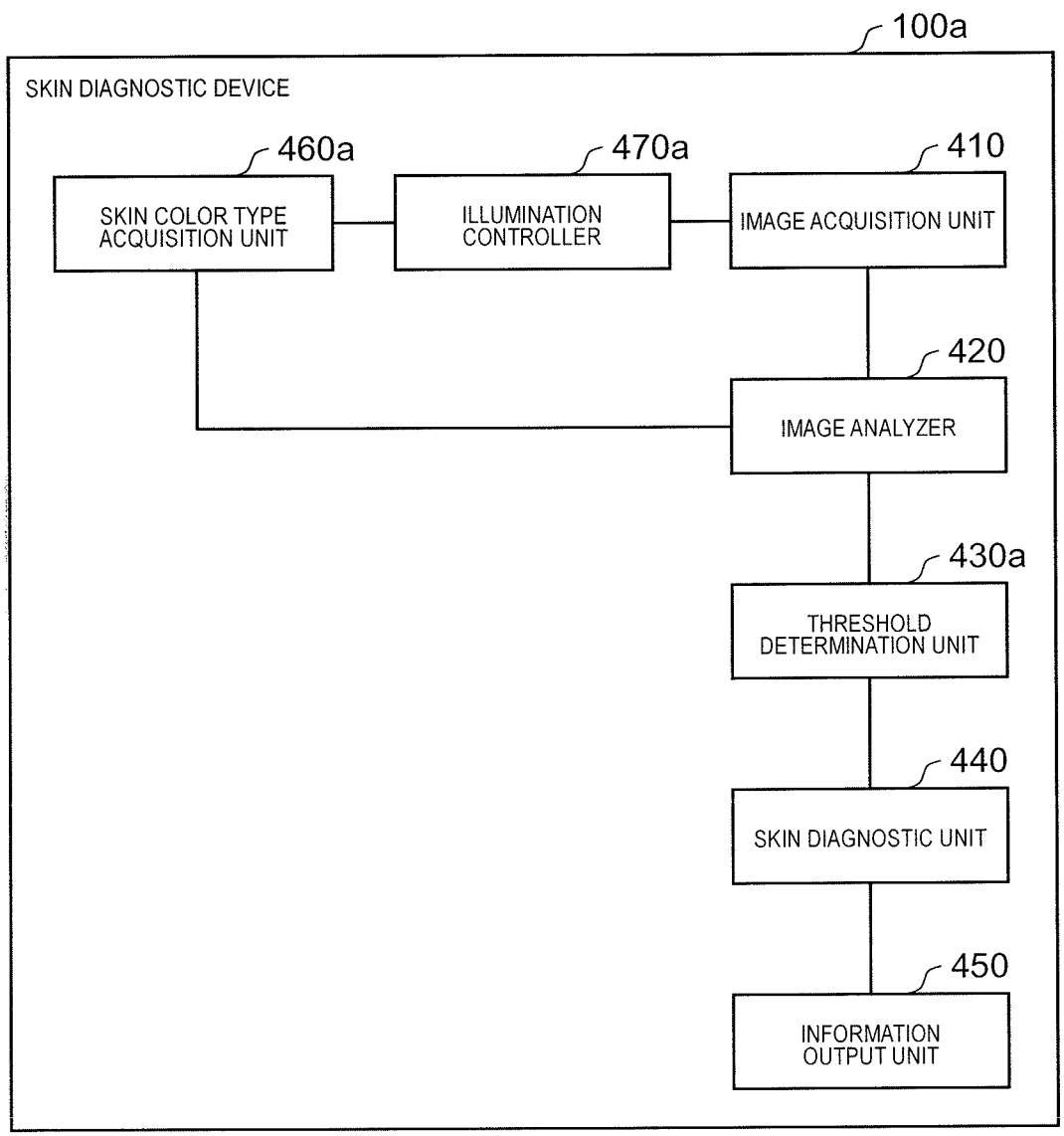
FIG. 20 is a block diagram showing an example of a configuration of the skin diagnostic device according to Embodiment 2.

FIG. 20 is a block diagram showing an example of the configuration of skin diagnostic device 100a and corresponds to FIG. 15 of Embodiment 1.

As shown in FIG. 20, in addition to the configuration shown in FIG. 15, skin diagnostic device 100a includes skin color type acquisition unit 460a and illumination controller 470a. In addition, skin diagnostic device 100a includes threshold determination unit 430a in place of threshold determination unit 430 shown in FIG. 15.

Skin color type acquisition unit 460a acquires the skin color type of the skin to be diagnosed and notifies illumination controller 470a and image analyzer 420 of the obtained skin color type. For example, skin color type acquisition unit 460a acquires a skin color type by generating above-described skin color type selection screen 150a (see FIG. 18) to display on display 120 and detecting the selection operation performed on the skin color type options on skin color type selection screen 150a.

Illumination controller 470a changes the light amount (brightness) of the illumination with respect to the skin as the target of the skin diagnosis according to the notified skin color type. Illumination controller 470a includes, for example, above-described illuminator 140a (see FIG. 18) and changes the brightness of illumination by controlling the output of illuminator 140a.

Figure 21:
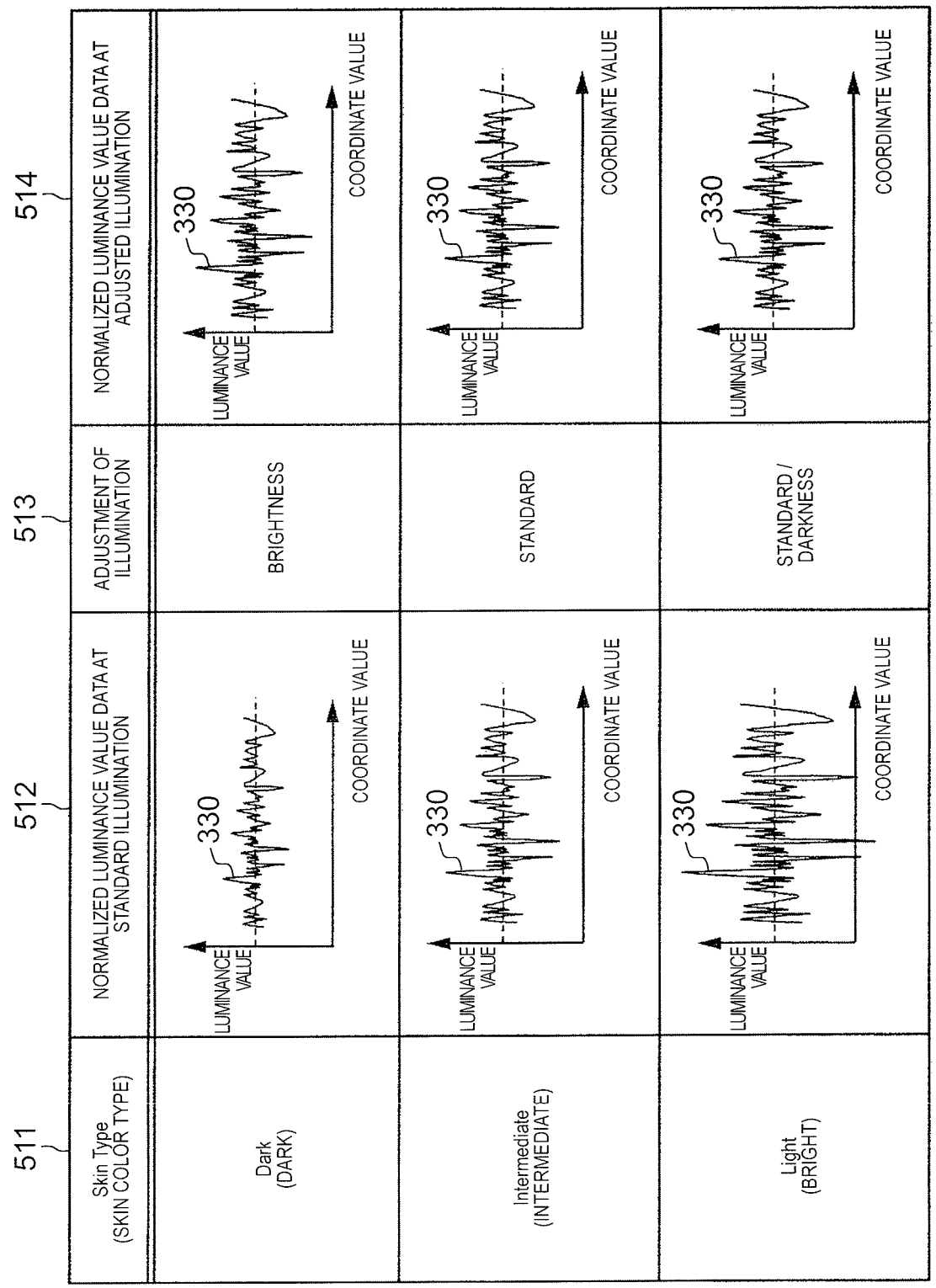
FIG. 21 is a diagram showing an example of illumination control according to a skin color type in Embodiment 2.

FIG. 21 is a diagram showing an example of illumination control according to the skin color type.

The skin color (lightness) of the ground greatly differs depending on race, age, living environment, and the like. As shown in FIG. 21, if skin color types 511 are different, for example, even if the darkness levels of the colors of the spots (the impression of the darkness of the discolored region visually recognized) are the same, the fluctuation width (contrast) of normalized luminance value data 330 (512) becomes larger as the skin color is brighter, and becomes smaller as the color of the skin is darker. If the fluctuation width of normalized luminance value data 330 is small, it is difficult to distinguish the noise from the spot portions, and if the fluctuation width of normalized luminance value data 330 is large, the luminance value is saturated and spot portions are excessively detected.

Therefore, illumination controller 470a performs illumination adjustment 513 that changes the brightness according to skin color type 511 by using the fact that as the capturing environment is brighter, the fluctuation width of normalized luminance value data 330 becomes larger and conversely, as the capturing environment is darker, the fluctuation width of normalized luminance value data 330 becomes smaller. That is, illumination controller 470a performs bright illumination for a dark skin color type, performs illumination with standard brightness for an intermediate skin color type, and performs standard or dark illumination for a bright skin color type.

For example, illumination controller 470a holds a value of an output control signal for illuminator 140a determined in advance by experiments or the like for each skin color type. Illumination controller 470a adjusts the illumination by outputting a signal with a value corresponding to the notified skin color type.

If the darkness levels of the colors of the spots are the same, skin image 310 shot with the illumination adjusted in such a manner is not affected by the flesh tone type, and the fluctuation width of the normalized luminance value data 330 (514) are equivalent.

Illumination controller 470a may obtain normalized luminance value data 300 in which the influence due to the darkness of the color of the skin is reduced by performing such illumination control. Illumination controller 470a synchronizes the timing of illumination with the timing of capturing by image acquisition unit 410. In addition, illumination controller 470a may control image acquisition unit 410 to adjust capturing conditions other than the illumination such as the shutter speed and the diaphragm of capturing unit 110 according to the skin color type.

Threshold determination unit 430a in FIG. 20 has the same function as image analyzer 420 in Embodiment 1. However, threshold determination unit 430a changes the determination method (that is, the determination method of threshold $B_{Th}$) for determining threshold coefficient α based on skewness S according to the notified skin color type.

Figure 22:
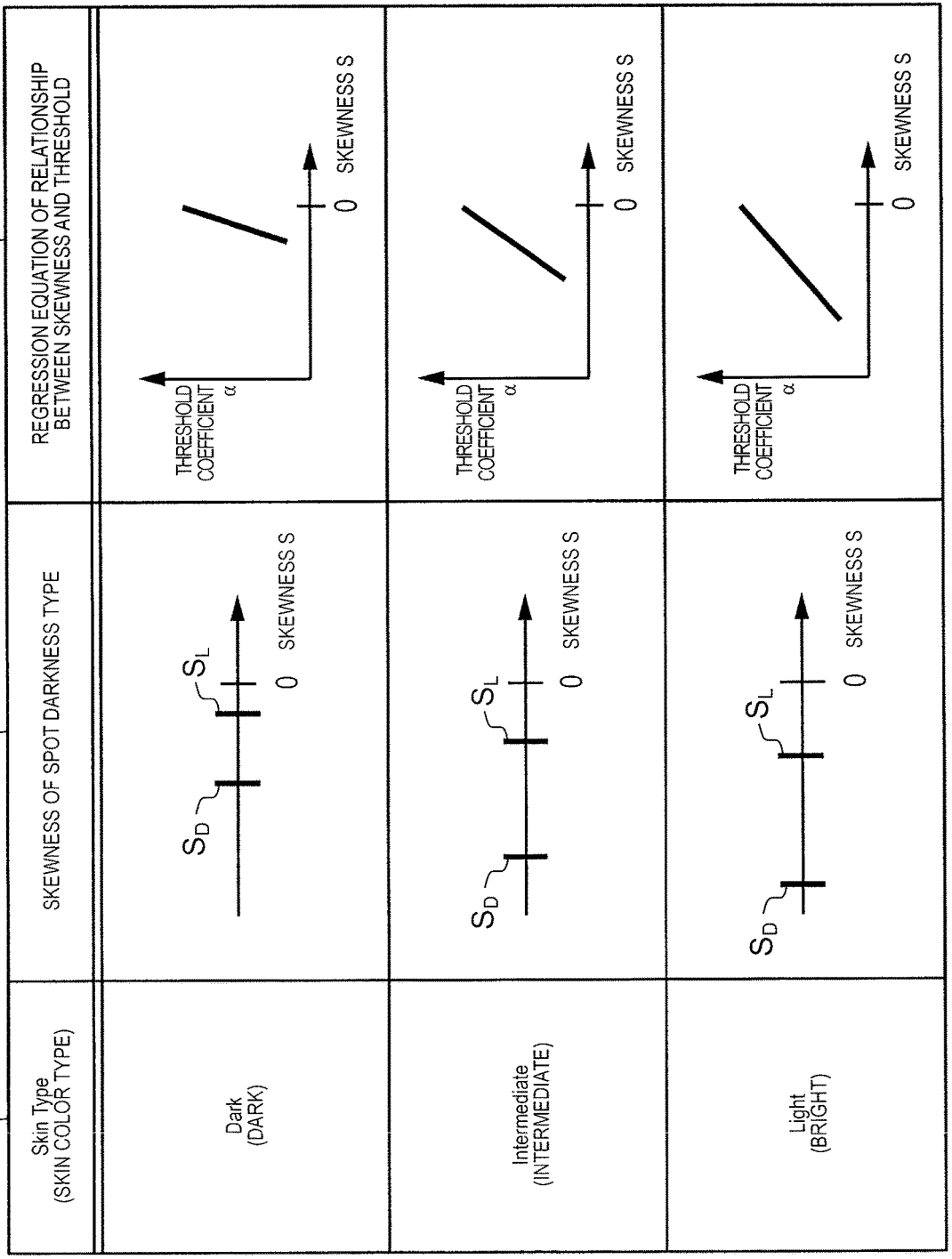
FIG. 22 is a diagram showing an example of threshold coefficient determination according to the skin color type in Embodiment 2.

FIG. 22 is a diagram showing an example of determination of threshold coefficient α according to the skin color type.

As shown in FIG. 22, even if skin color types 521 are different, skewness S (522) will be different even if the darkness levels of the colors of the spots (the impressions of the darkness of the discolored regions visually recognized) are the same. Both of skewness $S_L$ in a case where spots are light and skewness $S_D$ in a case where spots are darker increase in a negative direction as the skin color is brighter.

Therefore, threshold determination unit 430a adopts regression equation 523 (conversion rule 350) of the linear function of skewness S-threshold function α having different contents according to skin color type 521. That is, threshold determination unit 430a normalizes threshold function α with reference to the darkness level of the color of the spot by changing the above-described first positive value and/or the above-described second positive value with respect to regression equation 523 of skewness S-threshold function α. For example, threshold determination unit 430a holds a pair of first positive value and second positive value predetermined for each skin color type by experiments or the like.

As a result, threshold determination unit 430a may determine threshold function α as the same value if the darkness level of the color of the spot is the same regardless of the skin color type.

Skin diagnostic device 100a includes, for example, a CPU, a storage medium such as a ROM storing a control program, and a work memory such as a RAM. In this case, the functions of the above-described units are realized by the CPU executing the control program.

As a result of such operation, skin diagnostic device 100a may extract spot portion 370 by adjusting the brightness of illumination when imaging skin image 310 and the conversion method when converting skewness S into threshold $B_{Th}$ according to the darkness of the color of the skin to be diagnosed.

Operation of Device

Next, the operation of skin diagnostic device 100a will be described.

Figure 23:
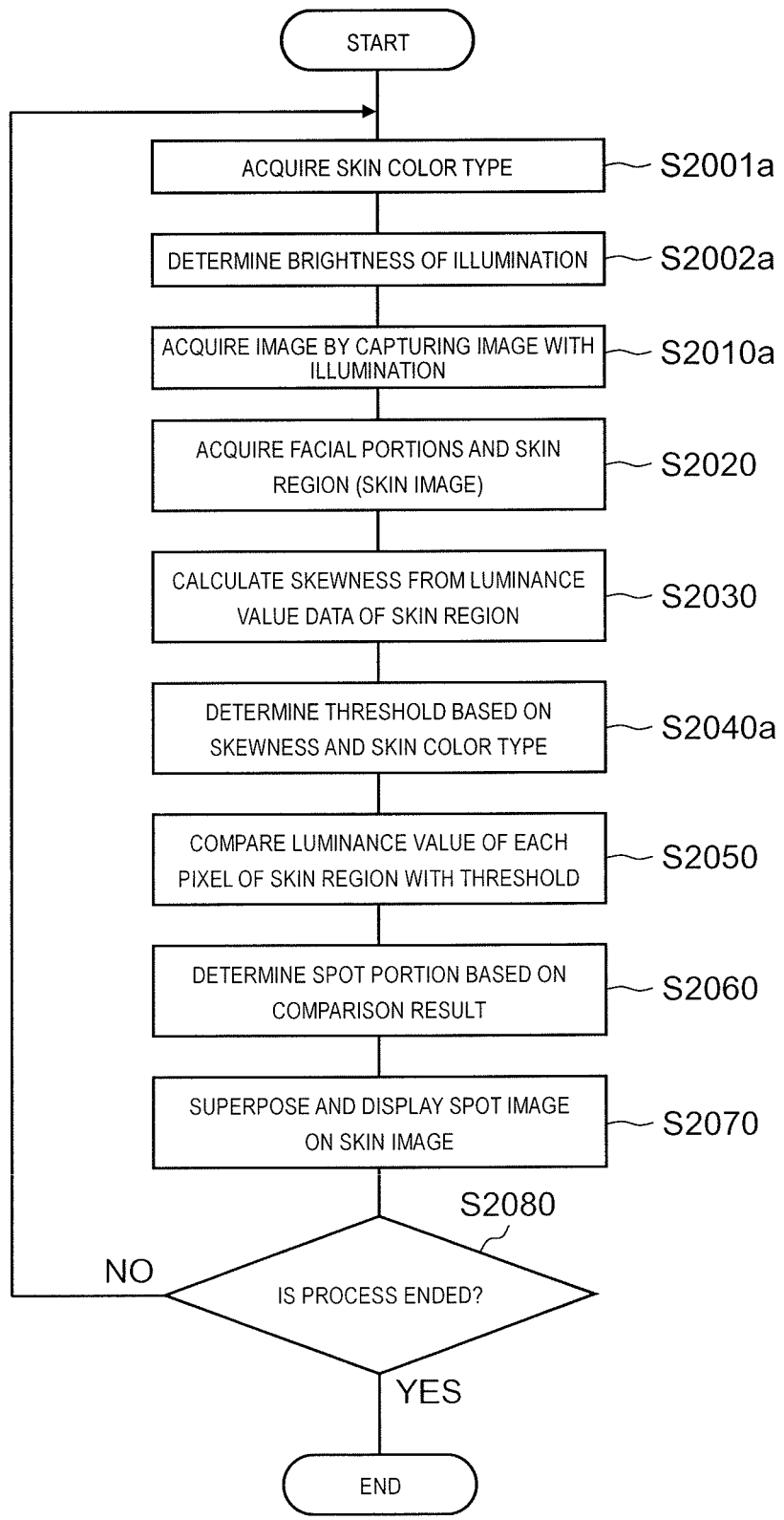
FIG. 23 is a flowchart showing an example of an operation of the skin diagnostic device according to Embodiment 2.

FIG. 23 is a flowchart showing an example of the operation of skin diagnostic device 100a and corresponds to FIG. 16 of Embodiment 1.

Prior to the process of step S2020 in FIG. 16, skin diagnostic device 100a performs the processes of steps S2001a to S2010a. In addition, skin diagnostic device 100a performs the process of step S2040a in place of the process of step S2040 of FIG. 16.

In step S2001a, skin color type acquisition unit 460a acquires the skin color type of the skin to be diagnosed.

In step S2002a, illumination controller 470a determines the brightness of the illumination for the skin based on the skin color type of the skin to be diagnosed.

In step S2010a, image acquisition unit 410 captures an image with the illumination of the determined brightness and acquires skin image 310.

In step S2040a, threshold determination unit 430a determines threshold $B_{Th}$ based on skewness S calculated from skin image 310 and the skin type.

As a result of such operation, skin diagnostic device 100a may extract spot portion 370 by adjusting the brightness of illumination when capturing skin image 310 and the conversion method when converting skewness S into threshold $B_{Th}$ according to the darkness of the color of the skin to be diagnosed. When mirror image 130 is a video, steps S2001a, S2010a, and S2030 to S2070 may be omitted as appropriate as in Embodiment 1.

Effect of Present Embodiment

As described above, skin diagnostic device 100a according to the present embodiment includes skin color type acquisition unit 460a that acquires the skin color type of the skin. Then, skin diagnostic device 100a includes illumination controller 470a that changes the brightness of the illumination for the skin according to the obtained skin color type, and threshold determination unit 430a that changes the method of determining threshold $B_{Th}$ based on standard value (skewness S) according to the obtained skin color type.

With such a configuration, skin diagnostic device 100a according to the present embodiment may perform a skin diagnosis that is less affected by the darkness of the skin color.

Modification Example of Present Embodiment

In the above-described Embodiment 2, the case where the relative position and the relative direction of illuminator 140a are fixed with respect to capturing unit 110 has been described, but the aspect of illuminator 140a is not limited thereto.

Figure 24:
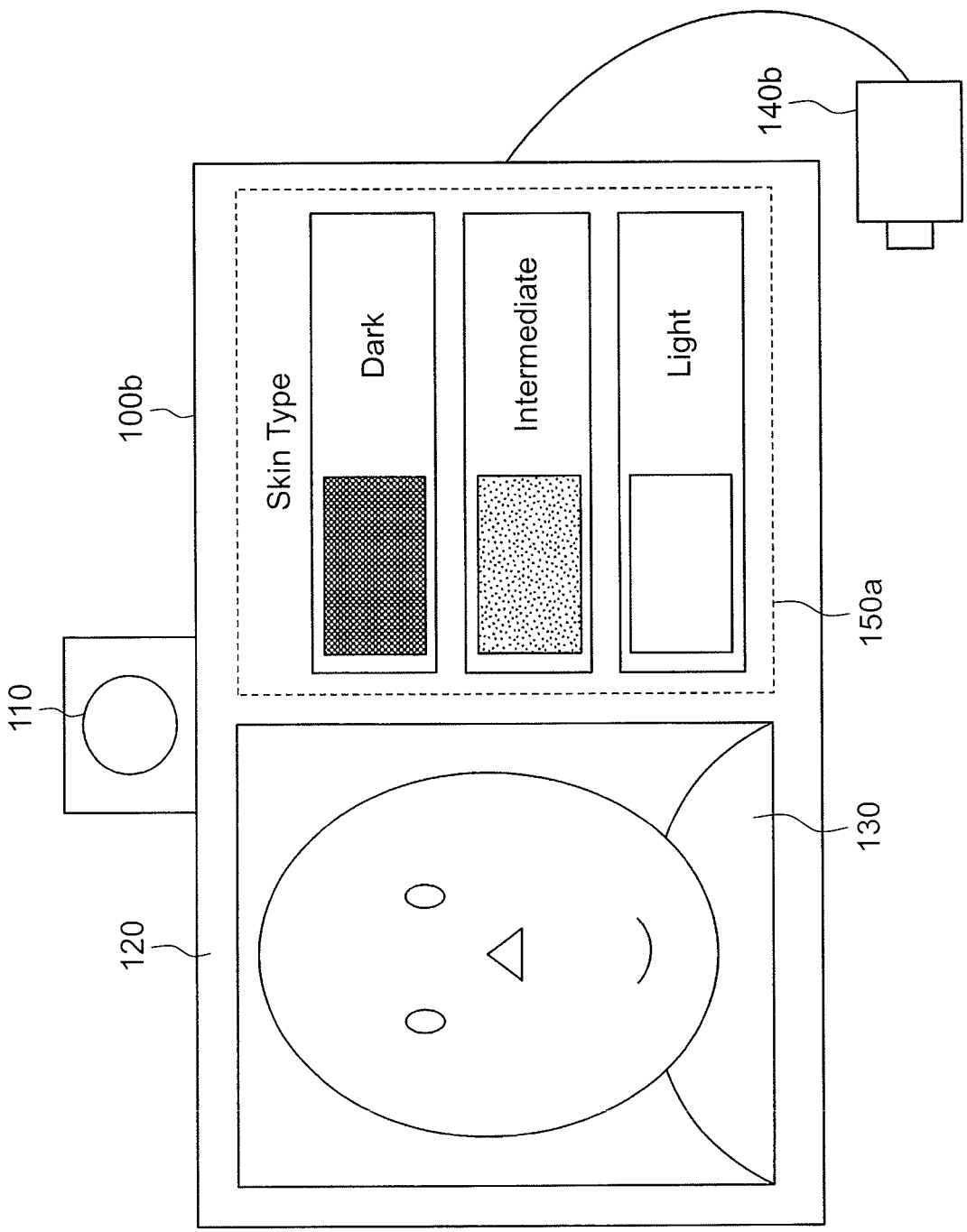
FIG. 24 is an example of an appearance of a skin diagnostic device according to a modification example of Embodiment 2.

FIG. 24 is a diagram showing an example of an external appearance of a skin diagnostic device according to a modification example and corresponds to FIG. 18. In addition, FIG. 25 is a diagram showing an example of the use state of the skin diagnostic device according to the modification example and corresponds to FIG. 19.

Figure 25:
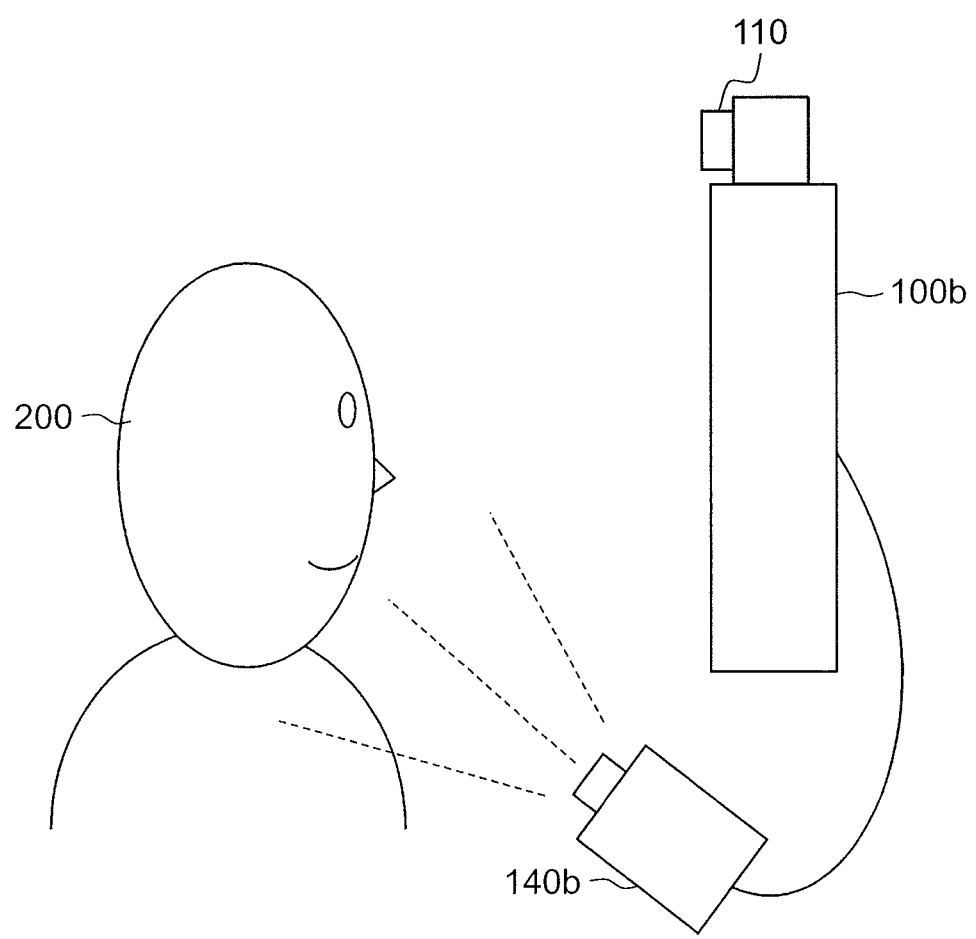
FIG. 25 is a diagram showing an example of a use state of the skin diagnostic device according to the modification example of Embodiment 2.

As shown in FIGS. 24 and 25, illuminator 140b may be, for example, a projector device having a high degree of freedom of position and direction which is connected to the main body of skin diagnostic device 100b in a wireless or wired manner. In this case, it is desirable that illumination controller 470a acquires the relative positional relationship between capturing unit 110, illuminator 140b, and face 200 and adjusts the light amount of illuminator 140b according to the obtained relative positional relationship. In addition, in a case where the directivity of the light of illuminator 140b is high, it is desirable that illumination controller 470a acquires information indicating the region of the eyes of the face from image analyzer 420 and sets the light radiated to the eyes to be lower (or to zero) than that of the other regions.

The method by which skin color type acquisition unit 460a acquires a skin color type is not limited to the above example. For example, skin color type acquisition unit 460a may determine the skin color type by image analysis of the captured image, for example, by comparing the color of the face portion with the color of a portion other than the face.

Skin diagnostic devices 100a and 100b may capture a skin image by using light of a specific wavelength such as polarized light or ultraviolet light according to the contents of the skin diagnosis.

A part of the configurations of skin diagnostic devices 100a and 100b may be physically separated from other parts of the configuration of the device. In this case, it is necessary for each of these separated parts to have a communicator for communicating with each other.

Summary of Present Disclosure

The skin diagnostic device of the present disclosure includes an image acquisition unit that acquires a skin image obtained by capturing skin, an image analyzer that calculates an index value indicating a darkness level of the color of a discolored region of the skin from the obtained skin image, a threshold determination unit that determines a threshold based on the calculated index value and a size of a contrast of the skin image, and a skin diagnostic unit that performs a diagnosis on the skin by comparing the determined threshold and normalized luminance value data obtained by normalizing luminance value data of the skin image with an average luminance value of the luminance value data.

In the skin diagnostic device, the index value may be a skewness indicating a degree of symmetry on a luminance value axis of a luminance value histogram of the skin image.

In the skin diagnostic device, the threshold determination unit may determine a lower value as the threshold as the skewness is higher and the contrast of the skin image is larger, and the skin diagnostic unit may determine that a portion in which the value of the normalized luminance value data is less than the threshold is the discolored region among one or a plurality of portions forming the skin image.

In the skin diagnostic device, the threshold determination unit may determine a higher value as a threshold coefficient as the skewness is higher and determines a value obtained by subtracting a multiplication value of a standard deviation of the normalized luminance value data and the determined threshold coefficient from the average luminance value as the threshold.

The skin diagnostic device may include a skin color type acquisition unit that acquires a skin color type of the skin and an illumination controller that changes brightness of the illumination with respect to the skin according to the obtained skin color type.

The skin diagnostic device may include a skin color type acquisition unit that acquires a skin color type of the skin, in which the threshold determination unit changes a method of determining the threshold based on the index value according to the obtained skin color type.

The skin diagnostic device may include an information presentation unit that superimposes and displays a spot image indicating the determined discolored region on the skin image.

In the skin diagnostic device, the skin analyzer may perform the diagnosis on each predetermined block of the skin image, and the image analyzer may calculate the skewness from an image range including the block and larger than the block in the skin image.

The skin diagnostic method of the present disclosure includes a step of acquiring a skin image obtained by capturing skin, a step of calculating an index value indicating a darkness level of the color of a discolored region of the skin from the obtained skin image, a step of determining a threshold based on the calculated index value and a size of a contrast of the skin image, and a step of performing a diagnosis on the skin by comparing the determined threshold and normalized luminance value data obtained by normalizing luminance value data of the skin image with an average luminance value of the luminance value data.

INDUSTRIAL APPLICABILITY

The skin diagnostic device and the skin diagnostic method according to the present disclosure are useful as a skin diagnostic device and a skin diagnostic method capable of performing a more stable skin diagnosis.

REFERENCE MARKS IN THE DRAWINGS 100, 100a SKIN DIAGNOSTIC DEVICE
110 CAPTURING UNIT
120 DISPLAY
140a ILLUMINATOR
150a SKIN TYPE SELECTION SCREEN
410 IMAGE ACQUISITION UNIT
420 IMAGE ANALYZER
430, 430a THRESHOLD DETERMINATION UNIT
440 SKIN DIAGNOSTIC UNIT
450 INFORMATION OUTPUT UNIT
460a SKIN COLOR TYPE ACQUISITION UNIT
470a LIGHTING CONTROLLER

The invention claimed is:

1. A skin diagnostic device comprising:
a memory that stores instructions; and
a processor, when executing the instructions stored in the memory, that performs operations including:
acquiring a skin image obtained by capturing skin;
determining a skewness indicating a degree of symmetry on a luminance value axis of a luminance value histogram of the skin image and indicating a darkness level of a color of a discolored region of the skin, from the acquired skin image;
determining a threshold based on the determined skewness and a size of a contrast of the skin image;
performing a diagnosis on the skin by comparing the determined threshold and normalized luminance value data obtained by normalizing luminance value data of the skin image with an average luminance value of the luminance value data;
determining that a portion in which a value of the normalized luminance value data is less than the threshold is the discolored region among one or a plurality of portions forming the skin image; and
generating a superimposed spot image and displaying the spot image indicating the determined discolored region on the skin image.

2. The skin diagnostic device of claim 1,
wherein the processor determines a lower value as the threshold as the skewness is higher and the contrast of the skin image is larger.

3. The skin diagnostic device of claim 2,
wherein the processor determines a higher value as a threshold coefficient as the skewness is higher and determines the threshold by subtracting a multiplication value of a standard deviation of the normalized luminance value data and the determined threshold coefficient from the average luminance value.

4. The skin diagnostic device of claim 1, wherein the processor further performs operations including:
   acquiring a skin color type of the skin; and
   changing brightness of illumination with respect to the skin according to the acquired skin color type.

5. The skin diagnostic device of claim 1, wherein the processor further performs operations including:
   acquiring a skin color type of the skin, and
   changing a method of determining the threshold based on the skewness according to the acquired skin color type.

6. The skin diagnostic device of claim 1,
   wherein the processor performs the diagnosis on each predetermined block of the skin image, and
   the processor determines the skewness from an image range including the block and larger than the block in the skin image.

7. A skin diagnostic method comprising:
   acquiring a skin image obtained by capturing skin;
   determining a skewness indicating a degree of symmetry on a luminance value axis of a luminance value histogram of the skin image and indicating a darkness level of a color of a discolored region of the skin, from the acquired skin image;
   determining a threshold based on the determined skewness and a size of a contrast of the skin image; and
   performing a diagnosis on the skin by comparing the determined threshold and normalized luminance value data obtained by normalizing luminance value data of the skin image with an average luminance value of the luminance value data;
   determining that a portion in which a value of the normalized luminance value data is less than the threshold is the discolored region among one or a plurality of portions forming the skin image; and
   generating a superimposed spot image and displaying the spot image indicating the determined discolored region on the skin image.

* * * * *